(12) United States Patent
Imai et al.

(10) Patent No.: US 11,189,809 B2
(45) Date of Patent: Nov. 30, 2021

(54) ORGANIC EL DEVICE AND DISPLAY UNIT

(71) Applicant: SONY CORPORATION, Tokyo (JP)

(72) Inventors: Toshiaki Imai, Kanagawa (JP); Emiko Kambe, Kanagawa (JP); Hideki Kobayashi, Kanagawa (JP); Jiro Yamada, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 620 days.

(21) Appl. No.: 15/529,009

(22) PCT Filed: Oct. 28, 2015

(86) PCT No.: PCT/JP2015/080356
§ 371 (c)(1),
(2) Date: May 23, 2017

(87) PCT Pub. No.: WO2016/088481
PCT Pub. Date: Jun. 9, 2016

(65) Prior Publication Data
US 2017/0271609 A1 Sep. 21, 2017

(30) Foreign Application Priority Data
Dec. 4, 2014 (JP) .............................. JP2014-245945

(51) Int. Cl.
| | |
|---|---|
| *H01L 51/54* | (2006.01) |
| *H01L 51/50* | (2006.01) |
| *C09K 11/06* | (2006.01) |
| *G09F 9/30* | (2006.01) |
| *H01L 27/32* | (2006.01) |
| *C07D 519/00* | (2006.01) |
| *C07D 401/14* | (2006.01) |
| *C07D 235/08* | (2006.01) |
| *C07D 401/04* | (2006.01) |
| *H01L 51/52* | (2006.01) |
| *C07D 235/20* | (2006.01) |
| *H01L 51/00* | (2006.01) |
| *C07D 235/18* | (2006.01) |
| *C07D 471/04* | (2006.01) |
| *H05B 33/12* | (2006.01) |
| *H05B 33/22* | (2006.01) |
| *C07C 15/28* | (2006.01) |

(52) U.S. Cl.
CPC ........ *H01L 51/5012* (2013.01); *C07D 235/08* (2013.01); *C07D 235/18* (2013.01); *C07D 235/20* (2013.01); *C07D 401/04* (2013.01); *C07D 401/14* (2013.01); *C07D 471/04* (2013.01); *C07D 519/00* (2013.01); *C09K 11/06* (2013.01); *G09F 9/30* (2013.01); *H01L 27/32* (2013.01); *H01L 51/0012* (2013.01); *H01L 51/0052* (2013.01); *H01L 51/0072* (2013.01); *H01L 51/50* (2013.01); *H01L 51/5004* (2013.01); *H01L 51/508* (2013.01); *H01L 51/5096* (2013.01); *H01L 51/5209* (2013.01); *H05B 33/12* (2013.01); *H05B 33/22* (2013.01); *C07C 15/28* (2013.01); *H01L 2251/558* (2013.01)

(58) Field of Classification Search
CPC .. C07D 235/08; C07D 235/18; C07D 235/20; C07D 401/00; C07D 401/02; C07D 401/04; C07D 401/10; C07D 401/14; C07D 471/00; C07D 471/02; C07D 471/04; C07D 471/10; C07D 471/14; C07D 519/00; C07C 15/28; H01L 51/0032; H01L 51/0012; H01L 51/0052; H01L 51/0072; H01L 51/50; H01L 51/508; H01L 51/5012; H01L 51/5016; H01L 51/5096; H01L 51/5004; H01L 51/5209; H01L 27/32; H05B 33/12; H05B 33/22
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| | | | | |
|---|---|---|---|---|
| 2004/0113545 A1* | 6/2004 | Pang | ................... | H01L 27/3246 313/504 |
| 2005/0233166 A1* | 10/2005 | Ricks | .................. | H01L 51/5036 428/690 |
| 2006/0284552 A1* | 12/2006 | Lee | ...................... | H01L 27/3209 313/506 |
| 2007/0252522 A1* | 11/2007 | Kondakov | .......... | H01L 51/5092 313/506 |
| 2008/0233387 A1* | 9/2008 | Kambe | ............... | H01L 51/0072 428/332 |
| 2011/0180801 A1* | 7/2011 | Yamazaki | ........... | H01L 27/3244 257/59 |

(Continued)

FOREIGN PATENT DOCUMENTS

| | | |
|---|---|---|
| JP | 2003-338377 A | 11/2003 |
| JP | 2011-508368 A | 3/2011 |

(Continued)

*Primary Examiner* — Andrew K Bohaty
(74) *Attorney, Agent, or Firm* — Chip Law Group

(57) ABSTRACT

An organic EL device of the disclosure includes: a first electrode and a second electrode; and an organic layer provided between the first electrode and the second electrode. The organic layer includes a light-emitting layer. The organic layer includes, between the first electrode and the light-emitting layer, a first layer that contains a polycyclic aromatic hydrocarbon compound having orientation, and a second layer that contains a larger amount of nitrogen element than the first layer.

12 Claims, 10 Drawing Sheets

(56) References Cited

U.S. PATENT DOCUMENTS

2013/0285022 A1* 10/2013 Su ..................... H01L 51/5092
257/40

FOREIGN PATENT DOCUMENTS

| JP | 2012-204793 | A | 10/2012 |
| JP | 2013-191533 | A | 9/2013 |
| JP | 2014-207105 | A | 10/2014 |
| WO | 2008/062773 | A1 | 5/2008 |
| WO | 2010/041605 | A1 | 4/2010 |

* cited by examiner

[ FIG. 1 ]
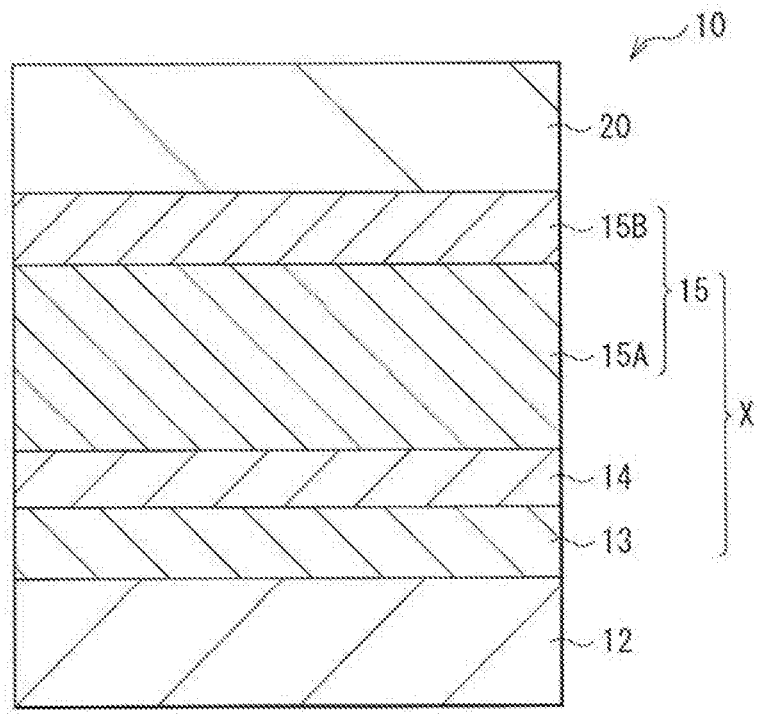
[ FIG. 2 ]
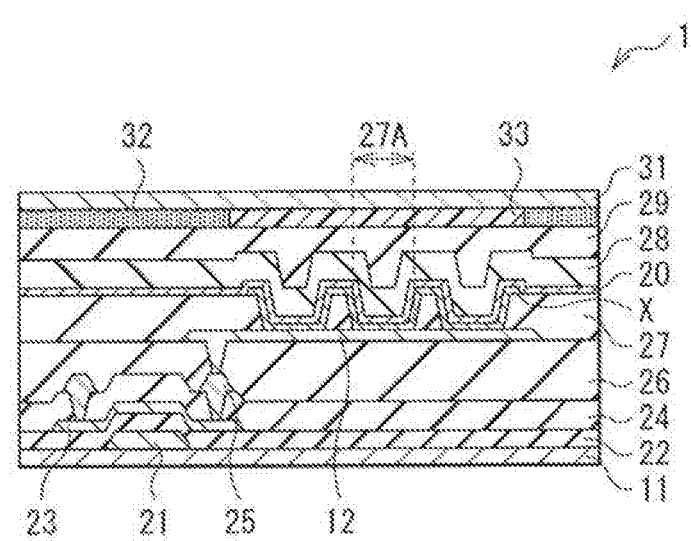

[FIG. 3]
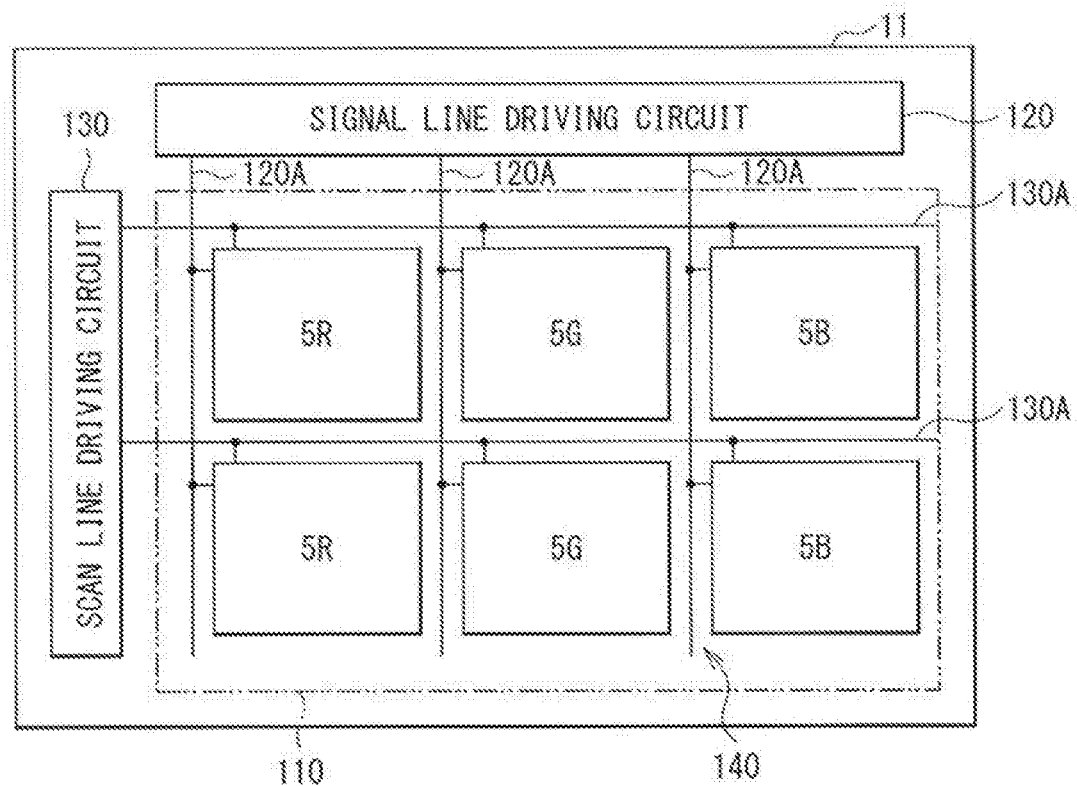
[FIG. 4]
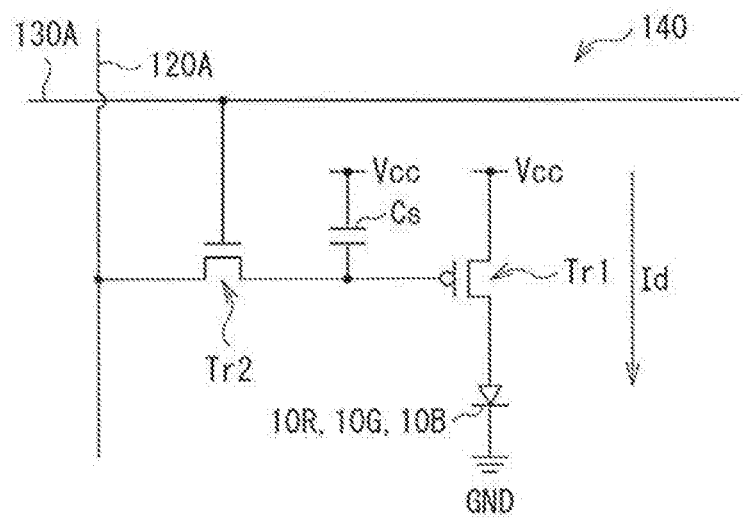

[FIG. 5A]
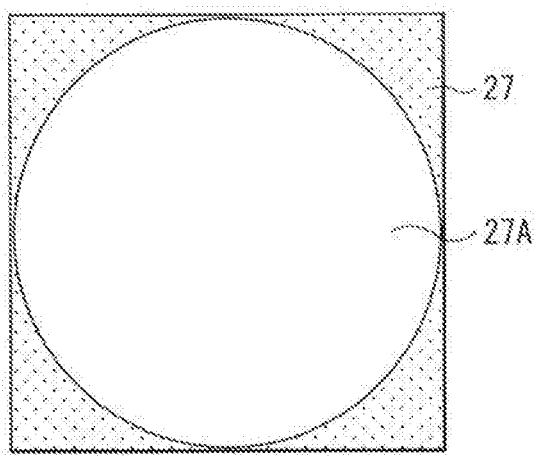
[FIG. 5B]
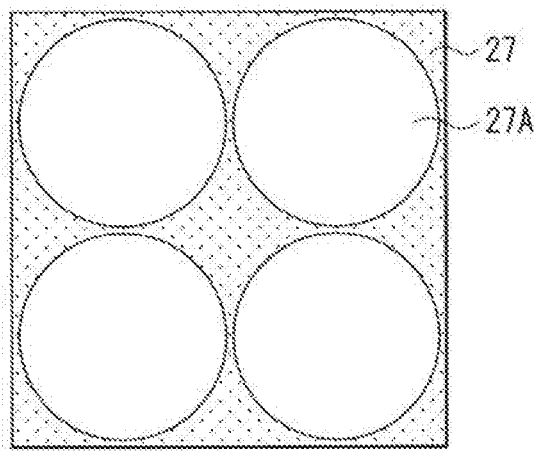
[FIG. 5C]
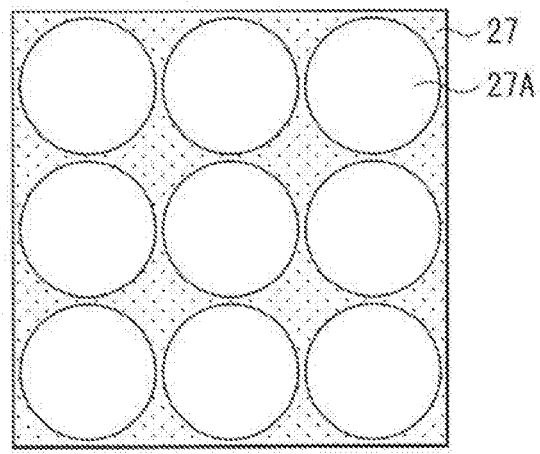

[ FIG. 6A ]
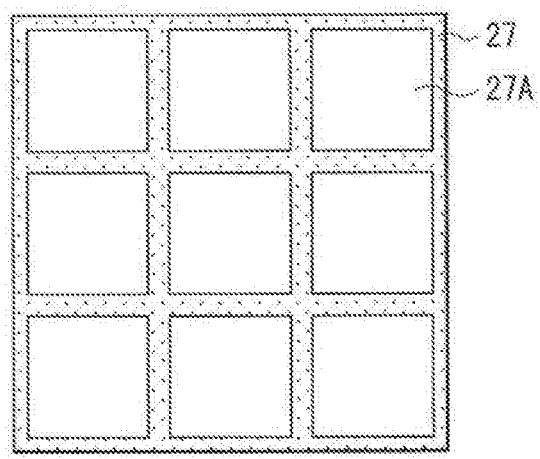
[ FIG. 6B ]
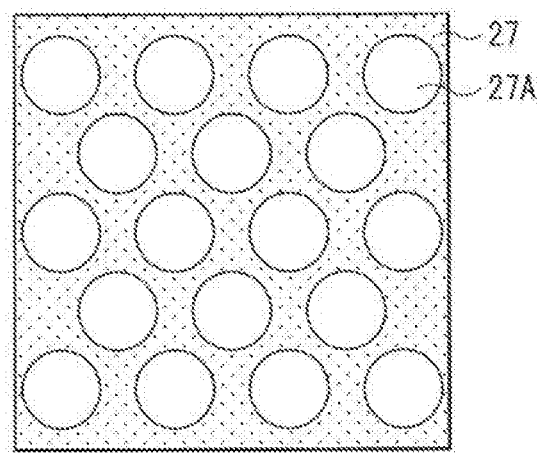

[ FIG. 7 ]
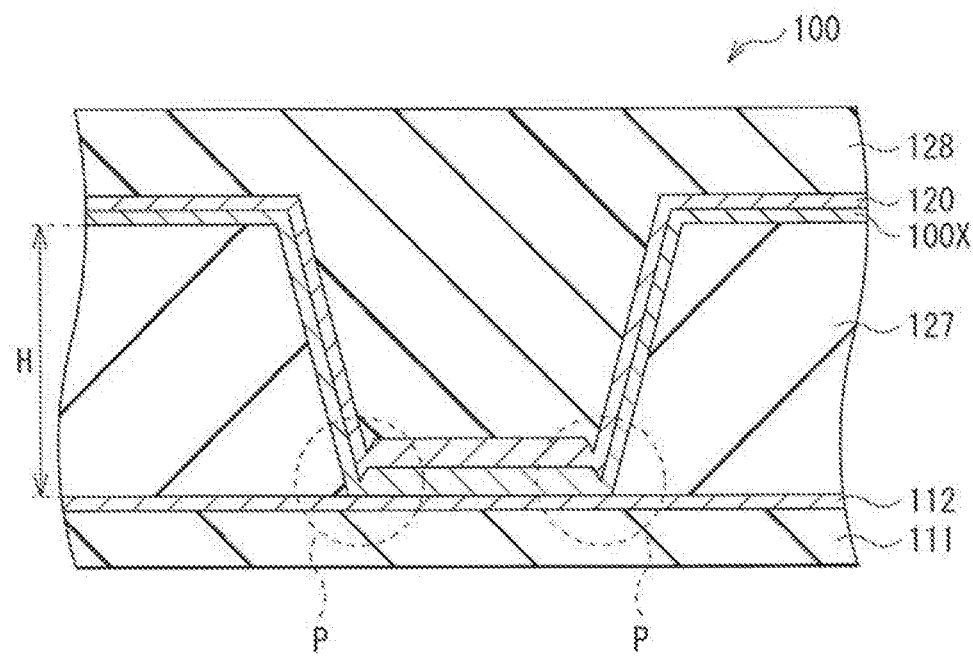
[ FIG. 8 ]
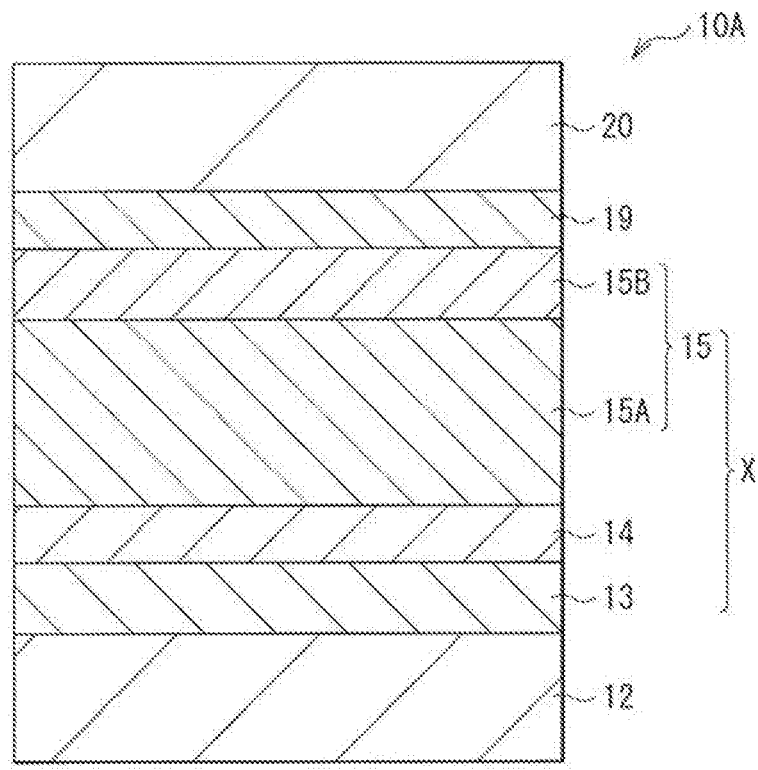

[FIG. 9]
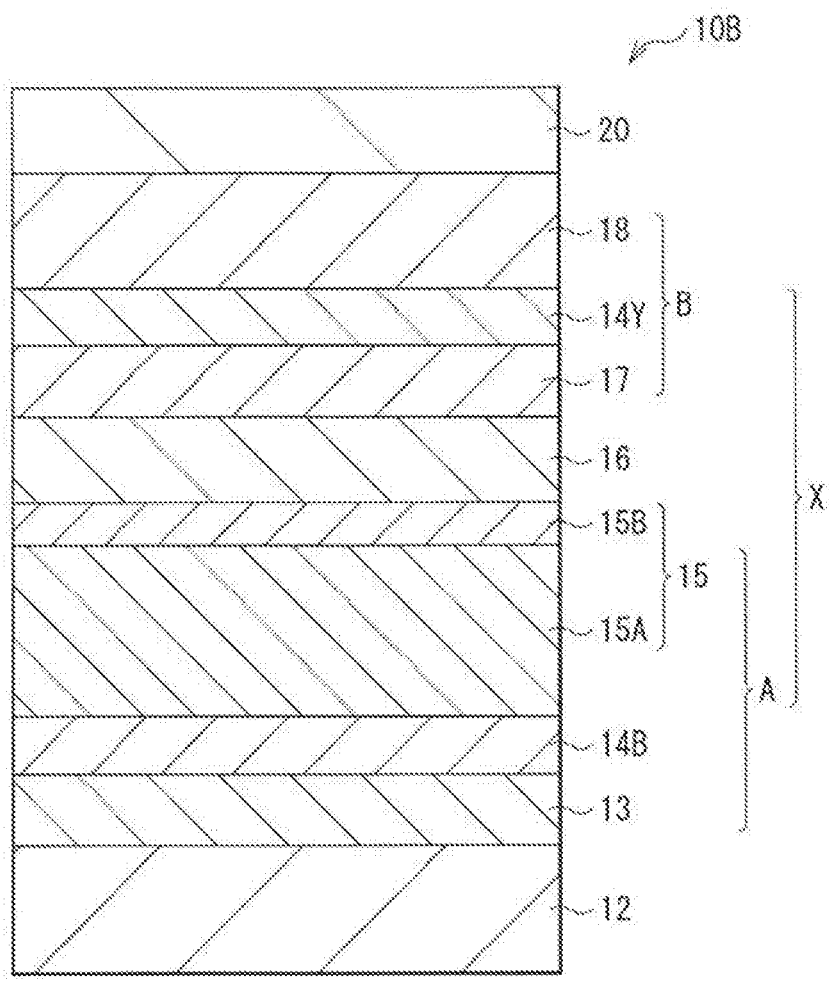

[ FIG. 10 ]
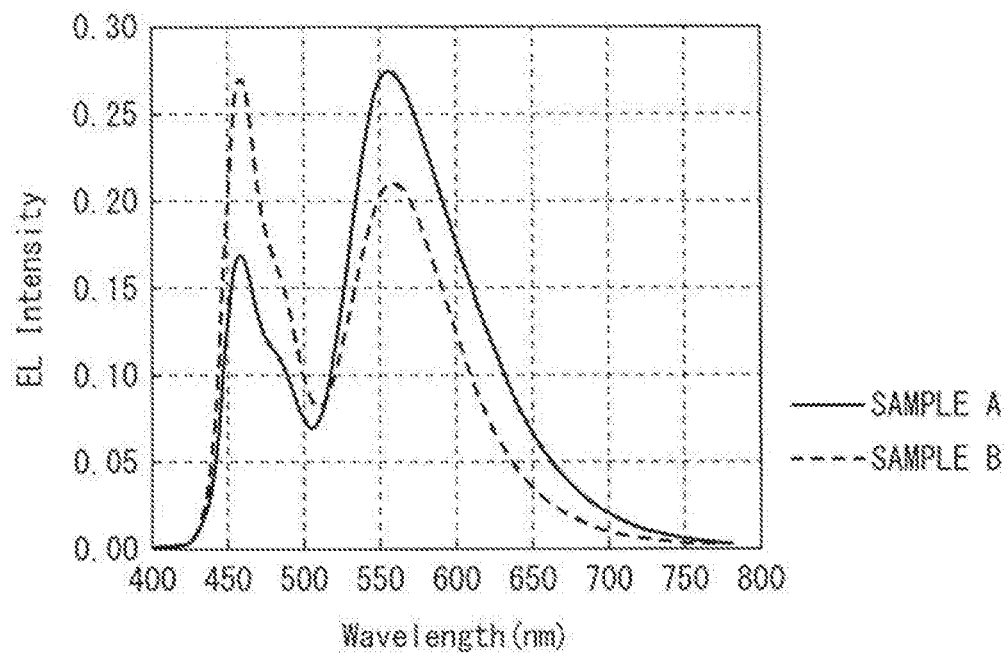
[ FIG. 11 ]
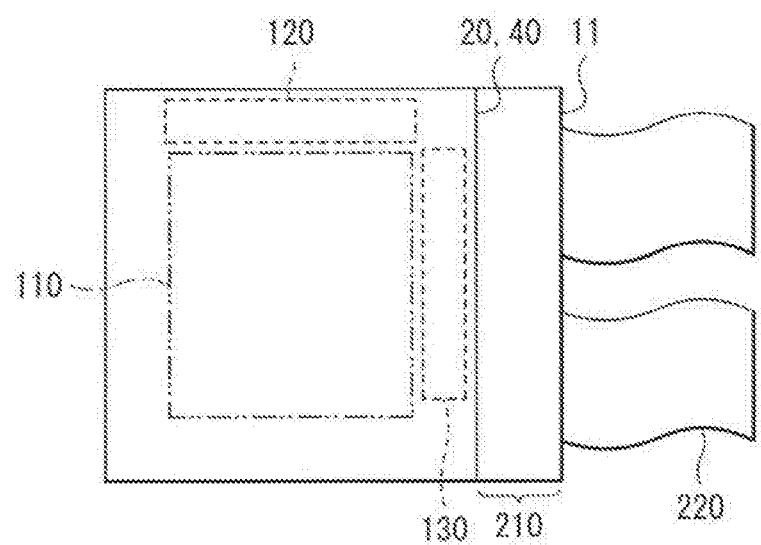

[ FIG. 12A ]
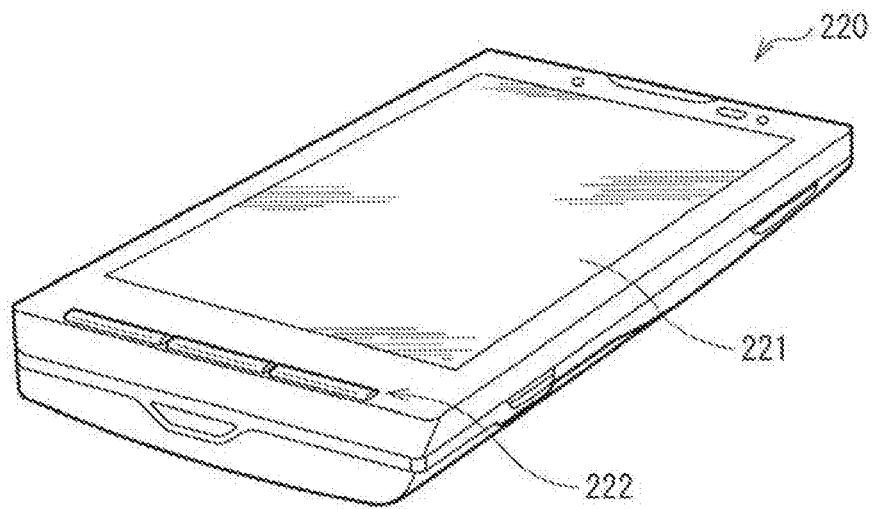
[ FIG. 12B ]
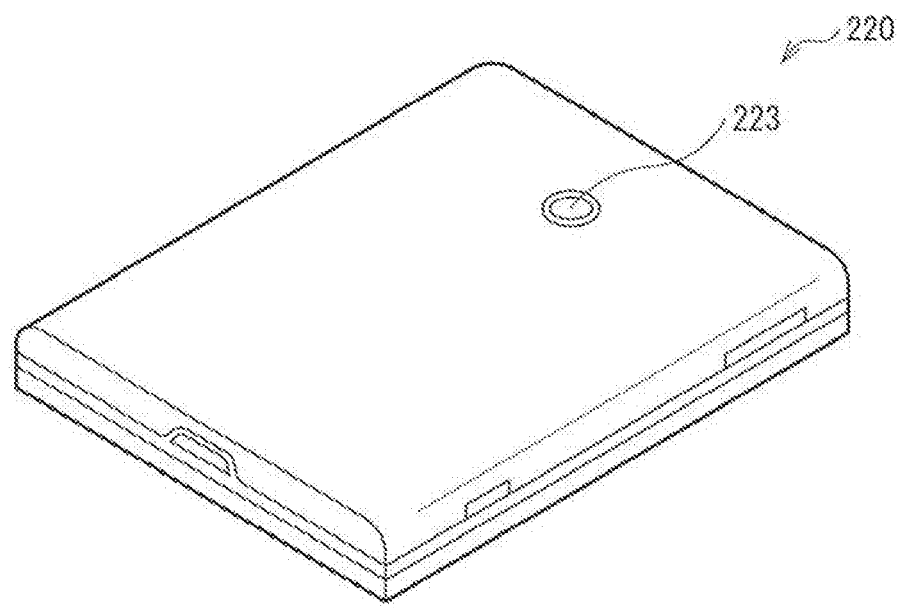

[FIG. 13A]
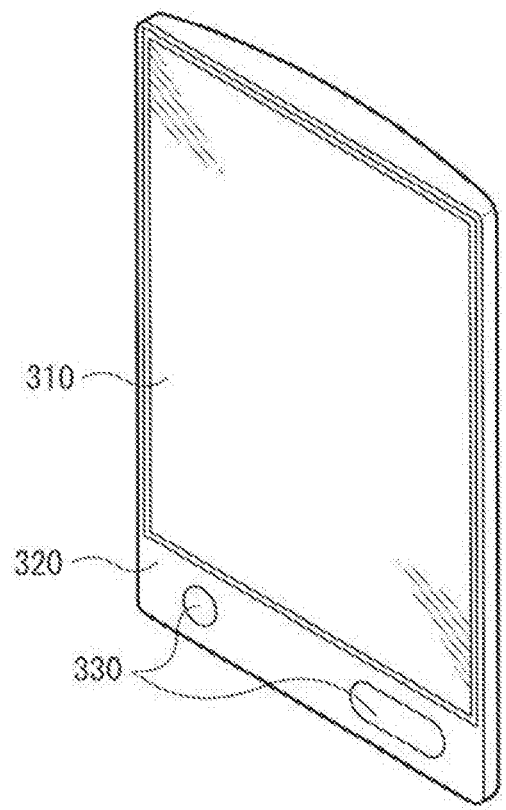
[FIG. 13B]
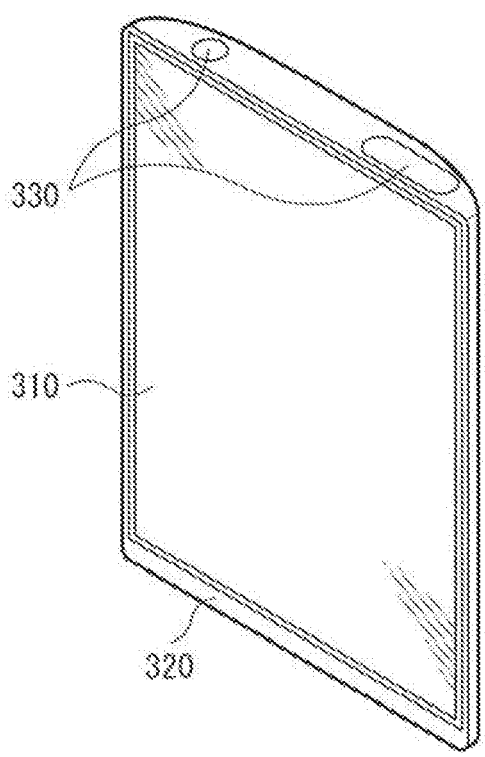

[FIG. 14]
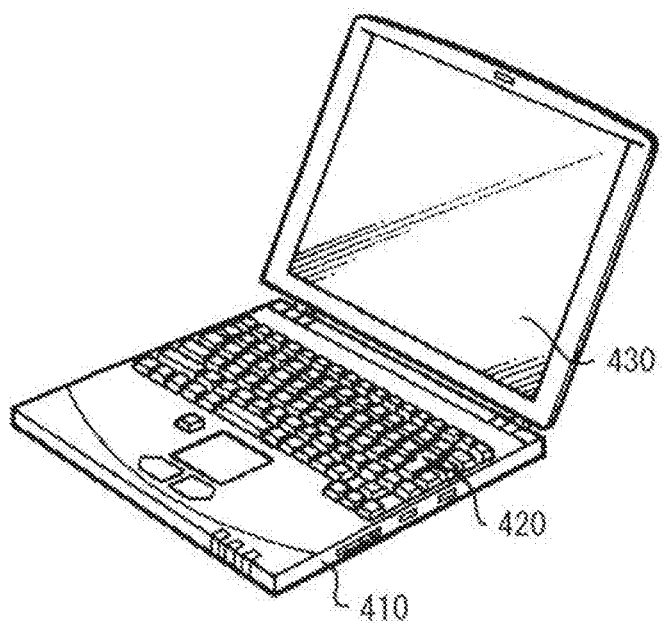

ORGANIC EL DEVICE AND DISPLAY UNIT

CROSS REFERENCE TO RELATED APPLICATIONS

This application is a U.S. National Phase of International Patent Application No. PCT/JP2015/080356 filed on Oct. 28, 2015, which claims priority benefit of Japanese Patent Application No. JP 2014-245945 filed in the Japan Patent Office on Dec. 4, 2014. Each of the above-referenced applications is hereby incorporated herein by reference in its entirety.

TECHNICAL FIELD

The disclosure relates to an organic electroluminescence (EL) device and a display unit that emit light utilizing an organic EL phenomenon.

BACKGROUND ART

In recent years, in the field of display units that perform image display, a display unit (organic EL (Electroluminescence) display unit) has been developed that uses, as a light-emitting device, a current-drive type optical device in which the emission luminance varies depending on a value of a flowing current, such as an organic EL device, and the product commercialization of such a display unit has been carried forward. Unlike a liquid crystal device, or any other equivalent device, such an organic EL device is a self-emitting device, thus eliminating the necessity for providing a light source (backlight) separately. Therefore, the organic EL display unit has the characteristics including the higher visibility of images, lower power consumption, and higher response speed of devices as compared with a liquid crystal display unit involving a light source.

The high image quality has been typically desired for the display units, and many different technologies for improvement of the image quality have been developed accordingly. For example, PTL 1 discloses a display unit including: a first member that propagates and emits light from light-emitting devices to the outside; and a second member that segments each of sub-pixels, in which the first member and the second member are made of materials having different refractive indexes from each other. In this display unit, the light propagating through the first member is reflected on the surface of the second member facing the first member, thereby improving the light extraction efficiency.

CITATION LIST

Patent Literature

[PTL 1] Japanese Unexamined Patent Application Publication No. 2013-191533

SUMMARY OF THE INVENTION

Meanwhile, an organic layer including a light-emitting layer is formed using a vapor deposition method, a film thickness (thickness) of the organic layer to be formed on a tapered surface such as a side surface of a partition becomes smaller by about one third to about one fifth in comparison with a thickness of the organic layer to be formed on a bottom surface. When an organic layer of the display unit disclosed in the above-described PTL 1 is formed using the vapor deposition method, a thickness of the organic layer in the vicinity of a boundary between a side surface of the second member and a bottom surface of a light emission region that is segmented by the side surface and the partition became smaller, and thus it has been likely that a leakage current occurs in a thin-film region of the organic layer, in particular, in the vicinity of the boundary between the side surface of the second member and the bottom surface of the light emission region, which may possibly cause deterioration in the current efficiency.

Accordingly, it is desirable to provide an organic EL device that makes it possible to improve the current efficiency, and a display unit that uses such an organic EL device.

An organic EL device according to one embodiment of the technology includes: a first electrode and a second electrode; and an organic layer provided between the first electrode and the second electrode. The organic layer includes a light-emitting layer. The organic layer includes, between the first electrode and the light-emitting layer, a first layer that contains a polycyclic aromatic hydrocarbon compound having orientation, and a second layer that contains a larger amount of nitrogen element than the first layer.

A display unit according to one embodiment of the technology includes a plurality of above-described organic EL devices In the organic EL device and the display unit provided with the organic EL device according to the respective embodiments of the technology, the first layer that contains the polycyclic aromatic hydrocarbon compound having the orientation, and the second layer that contains a larger amount of nitrogen element than the first layer are provided between the first electrode and the light-emitting layer. This improves flow of electrical charges between the first electrode and the light-emitting layer.

In the organic EL device and the display unit provided with the organic EL device according to the respective embodiments of the technology, the first layer that contains the polycyclic aromatic hydrocarbon compound having the orientation, and the second layer that contains a larger amount of nitrogen element than the first layer are provided between the first electrode and the light-emitting layer, which improves flow of electrical charges between the first electrode and the light-emitting layer. This makes it possible to reduce generation of a leakage current, and to improve the current efficiency. It is to be noted that effects described above are not necessarily limitative, and any of effects described in the disclosure may be provided.

BRIEF DESCRIPTION OF DRAWINGS

FIG. 1 is a cross-sectional view of an organic EL device according to one embodiment of the disclosure.

FIG. 2 is a cross-sectional view of a display unit provided with the organic EL device illustrated in FIG. 1.

FIG. 3 is a plan view of a configuration of the display unit illustrated in FIG. 2.

FIG. 4 is a diagram illustrating an example of a pixel driving circuit illustrated in FIG. 3.

FIG. 5A is a plan view of an example of a configuration of a sub-pixel in the display unit illustrated in FIG. 2.

FIG. 5B is a plan view of another example of a configuration of the sub-pixel in the display unit illustrated in FIG. 2.

FIG. 5C is a plan view of still another example of a configuration of the sub-pixel in the display unit illustrated in FIG. 2.

FIG. 6A is a plan view of further still another example of a configuration of the sub-pixel in the display unit illustrated in FIG. 2.

FIG. 6B is a plan view of further still another example of a configuration of the sub-pixel in the display unit illustrated in FIG. 2.

FIG. 7 is a cross-sectional view of an organic EL device as a comparative example of the disclosure.

FIG. 8 is a cross-sectional view of an organic EL device according to a modification example 1 of the disclosure.

FIG. 9 is a cross-sectional view of an organic EL device according to a modification example 2 of the disclosure.

FIG. 10 is a characteristic diagram illustrating improvement of the emission intensity of the organic EL device of the disclosure.

FIG. 11 is a plan view of a simplified configuration of a module including the above-described display unit.

FIG. 12A is a perspective view of an appearance of a smartphone of an application example 1 of the disclosure when viewed from front.

FIG. 12B is a perspective view of an appearance of the smartphone illustrated in FIG. 11A when viewed from back.

FIG. 13A is a perspective view of an example of an appearance of a tablet of an application example 2 of the disclosure.

FIG. 13B is a perspective view of another example of an appearance of the tablet of the application example 2 of the disclosure.

FIG. 14 is a perspective view of an appearance of an application example 3 of the disclosure.

MODES FOR CARRYING OUT THE INVENTION

Hereinafter, some embodiments of the disclosure are described in detail with reference to the drawings. The description is given in the following order.
1. Embodiment
(An example of having an electron supply layer including two layers between a light-emitting layer and a cathode)
1-1. Basic Configuration
1-2. Display Unit
2. Modification Examples
2-1. Modification Example 1 (an example of providing a metal doped layer between the electron supply layer and the cathode)
2-2. Modification Example 2 (an example of having a tandem structure in which two light-emitting layers are laminated)
3. Working Examples
4. Application Examples
[1. Embodiment]
(1-1. Basic Configuration)

FIG. 1 illustrates a cross-sectional configuration of an organic EL device 10 according to one embodiment of the disclosure, and FIG. 2 illustrates a cross-sectional configuration of a display unit 1 of the disclosure. The display unit 1, which is used as an organic EL television apparatus, or any other similar apparatus, is a top-surface light emission (top-emission) display unit that extracts emission light arising in recombining holes injected from an anode and electrons injected from a cathode 20 inside light-emitting layers (a blue light-emitting layer 14 and a yellow light-emitting layer 18) from the opposite side of a drive substrate 11 (from the side of a counter substrate 31). Further, the display unit 1 extracts any of color light of R (red), G (green), and B (blue) with use of, for example, the organic EL device 10 that emits white light, and a color filter 33. The organic EL device 10 has a configuration of laminating, for example, an anode 12, an organic layer X, and the cathode 20 in this order on the drive substrate 11. Among these, in the organic layer X, for example, a hole supply layer 13, a light-emitting layer 14, and an electron supply layer 15 are laminated in this order from the anode 12 side.

In the present embodiment, the electron supply layer 15 has a configuration in which a first layer 15A that contains a polycyclic aromatic hydrocarbon compound having the orientation, and a second layer 15B that contains a larger amount of nitrogen element than the first layer 15A are laminated.

Further, in the present embodiment, a plurality of openings 27A each of which is provided by an insulating film configuring a partition 27 are provided on the anode 12 that is independently provided for each of sub-pixels 5R, 5G, and 5B configuring a pixel.

The drive substrate 11 is a support member on which the organic EL devices 10 are formed in an array on one main-surface side thereof. A constituent material of the drive substrate 11 is any heretofore known material, and for example, a film, sheet, or any other similar comparable material that is made of quartz, glass, metal foil, or resin material is used. Above all, quartz and glass may be preferable. Examples of the resin materials include: methacrylate resin as represented by polymethylmethacrylate (PMMA); polyester such as polyethylene terephthalate (PET), polyethylene naphthalate (PEN), and polybutylene naphthalate (PBN); polycarbonate resin; or any other equivalent material. However, it is necessary to adopt a laminated structure or perform surface treatment to suppress water or gas permeability.

A gate electrode 21 is provided on the drive substrate 11. The gate electrode 21 is made of, for example, molybdenum (Mo), or any other equivalent material. On the drive substrate 11 and the gate electrode 21, an insulating layer 22 is provided. The insulating layer 22 is made of, for example, silicon oxide ($SiO_2$), silicon nitride ($SiN_x$), or any other equivalent material. On the insulating layer 22, a channel layer 23 is provided at a region corresponding to the gate electrode 21. The gate electrode 21 and the channel layer 23 serve to configure a drive transistor DRTr (for example, Tr1 in FIG. 4), or any other element. It is to be noted that, in this example, the transistor is configured in the so-called bottom-gate structure in which the channel layer 23 is provided on the top of the gate electrode 21; however, the configuration is not limited thereto. Alternatively, the transistor may be configured in the so-called top-gate structure in which the channel layer is provided on the bottom of the gate electrode. On the channel layer 23 and the insulating layer 22, there is provided an insulating layer 24. The insulating layer 24 is made of, for example, a material similar to a material of the insulating layer 22. Further, at a portion of a region where the channel layer 23 is provided, a pair of source and drain electrodes 25 are provided to pass through the insulating layer 24. The source and drain electrodes 25 may include three layers of titanium (Ti)/aluminum (Al)/titanium (Ti), for example. On the insulating layer 24 and the source and drain electrodes 25, there is provided an insulating layer 26. The insulating layer 26 is made of, for example, polyimide resin, acrylic resin, or any other equivalent material. On the insulating layer 26, openings 26A is provided, and electrical connection is made between the anode 12 to be hereinafter described and the source and drain electrodes 25 related to a source electrode of a drive transistor DTr.

For the anode 12, to efficiently inject holes into the light-emitting layer 14, it may be preferable to use a constituent material having a large work function from the vacuum level of an electrode material. Specifically, for example, chromium (Cr), gold (Au), alloy of tin oxide ($SnO_2$) and antimony (Sb), alloy of zinc oxide (ZnO) and aluminum (Al), silver (Ag) alloy, oxide of any of those metal or alloy materials, or any other equivalent material may used independently or in a mixed state.

Further, the anode 12 may be configured in a laminated structure including a layer with the superior light reflectivity (lower layer) and a layer having the light-transmissive performance and a large work function (upper layer) that is provided on the top of the lower layer. For a constituent material of the lower layer, it may be preferable to use alloy containing Al as a major constituent. As an accessory constituent, any element having a relatively smaller work function than Al serving as a major constituent is used. As such an accessory constituent, it may be preferable to use lanthanoid-series elements. The lanthanoid-series elements are not large in the work function: however, inclusion of those elements improves both the stability of anodes and the hole-injecting performance of the anodes. Alternatively, as the accessory constituent, any of other elements such as silicon (Si) and copper (Cu) may be used other than the lanthanoid-series elements.

A contained amount of the accessory constituent in an Al alloy layer configuring the lower layer may be preferably about 10 wt % or less in total if a material such as neodymium (Nd), nickel (Ni), and titanium (Ti) that serves to stabilize Al is used, for example. This makes it possible to maintain the reflectance in the Al alloy layer, and to keep the Al alloy layer in a stable state in the manufacturing process of the organic EL device. Further, this ensures that the processing accuracy and chemical stability are achieved. Moreover, the conductivity of the anode 12, and adhesion between the anode 12 and the drive substrate 11 are also improved. It is to be noted that the above-described metal materials such as Nd are small in the work function, and therefore a hole-injecting barrier becomes larger if an amine-based material that is generally used for the hole supply layer 13 to be described later is used. In this case, in such a manner that a layer mixing an acceptor material such as 7,7,8,8-tetracyano-2,3,5,6-tetrafluoroquinodimethane (F4-TCNQ) with the amine-based material, or a p-doped layer using a material such as polyethylene dioxithiophene-polystyrene sulfonate (PEDOT-PSS) is formed at an interface of the anode 12, it is possible to reduce the hole-injecting barrier, and to suppress a rise in a drive voltage. Other than the above-described manner, the use of the azatriphenylene derivative to be hereinafter described allows the elements to be stabilized while suppressing a rise in the drive voltage.

For a constituent material of the upper layer, oxide of Al alloy, oxide of molybdenum (Mo), oxide of zirconium (Zr), oxide of Cr, and oxide of tantalum (Ta) may be used. For example, if the upper layer is an oxide layer of Al alloy (including a natural oxide film) that contains the lanthanoid-series elements as the accessory constituent, oxides of the lanthanoid-series elements have high optical transmittance, and thus the optical transmittance of the upper layer containing such oxides becomes favorable. As a result, the reflectance on the surface of the lower layer is kept at high level. Further, the use of a transparent conductive layer of a material such as ITO (Indium Tin Oxide) and IZO (Indium Zinc Oxide) as the upper layer improves the electron-injecting characteristics of the anode 12. It is to be noted that each of the ITO and IZO has a large work function, and therefore, it is possible to raise the carrier-injecting efficiency, and to improve the adhesion between the anode 12 and the drive substrate 11 by using the ITO or IZO for the layer that comes in contact with the drive substrate 11, that is, the lower layer.

It is to be noted that, in a case where a drive method of the display unit that is configured with use of the organic EL device 10 is an active-matrix method, the anode 12 is provided in a state of being patterned on each pixel basis and being coupled to the drive transistor DRTr that is provided on the drive substrate 11. In this case, a configuration is made in which the partition 27 is provided on the anode 12, and the surface of the anode 12 of each pixel is exposed from the opening 27A of the partition 27.

The partition 27 serves to assure the insulating performance of the anode 12 and the cathode 20, and to define a desired shape of a light-emitting region. Further, the partition 27 also has a function as a partition to be used at the time of coating with use of an ink-jet method, a nozzle-coating method, or any other equivalent method in the manufacturing process. The partition 27 is made of, for example, an inorganic insulating material such as $SiO_2$, or a photosensitive resin material such as positive-type photosensitive polybenzoxazole and positive-type photosensitive polyimide. On the partition 27, the opening 27A (for example, see FIG. 5A) is provided corresponding to the light-emitting region. In the present embodiment, the plurality of openings 27A are provided on the single anode 12, as illustrated in FIGS. 5B and 5C, for example. It is to be noted that, in these examples, the openings 27A are illustrated in circular shapes; however, this is not limitative. For example, as illustrated in FIG. 6A, the openings 27A may have rectangular shapes alternatively. Further, placement locations of the openings 27A are also not limited specifically. For example, the so-called close packing layout may be adopted as illustrated in FIG. 6B. It is to be noted that an inclined angle of a side surface (inclined surface) of the opening 27A relative to an electrode surface of the anode 12 may be preferably 45 degrees or more, for example.

The hole supply layer 13 is a buffer layer to improve the efficiency of injecting holes into the light-emitting layer 14, and to prevent leakage. A thickness of the hole supply layer 13 may be preferably, for example, at least 5 nm but no more than 60 nm depending on an overall configuration of the organic EL device 10, in particular, the relation with the electron supply layer 15 to be hereinafter described.

A constituent material of the hole supply layer 13 may be selected as appropriate in terms of materials of the electrodes (the anode 12 and the cathode 20) and of the adjoining layers. Examples of the constituent material include benzin, styryl amine, triphenylamine, porphyrin, triphenylene, azatriphenylene, tetracyanoquinodimethane, triazole, imidazole, oxadiazole, polyarylalkane, phenylenediamine, arylamine, oxazole, anthracene, fluorenone, hydrazone, stilben, or any of derivatives of those materials, or heterocyclic conjugate-based monomer, oligomer, or polymer such as polysilane-based compound, vinylcarbazole-based compound, thiophene-based compound, or aniline-based compound. Any of the above-described materials may be used as the constituent material.

Further, examples of the specific material include α-naphthylphenylphenylenediamine, porphyrin, metallic tetraphenylporphyrin, metallic naphthalocyanine, hexacyanoazatriphenylene, 7,7,8,8-tetracyanoquinodimethane (TCNQ), F4-TCNQ, tetracyano 4,4,4-tris (3-methylphenylphenylamino) triphenylamine, N, N, N', N'-tetrakis (p-tolyl)

p-phenylenediamine, N, N, N', N'-tetraphenyl-4,4'-diaminobiphenyl, N-phenylcarbazole, 4-di-p-tolylaminostilbene, poly (paraphenylenevinylene), poly (thiophenevinylene), and poly (2,2'-thienylpyrrole).

The light-emitting layer 14 is a region in which holes injected from the anode 12 side and electrons injected from the cathode 20 side are recombined when an electric field is applied to the anode 12 and the cathode 20. Preferably, a constituent material of the light-emitting layer 14 may have a charge-injecting function (function of enabling to inject holes from the anode 12 or the hole supply layer 13 when an electric field is applied, and to inject electrons from the cathode 20 or the electron supply layer 15), a transport function (function of transporting the injected holes and electrons using force of an electric field), and a light-emitting function (function of providing a field for recombination of electrons and holes, leading to light emission).

The light-emitting layer 14 is made of, for example, a mixture material with a low-molecular material added to a polymer light-emission material in the case of, for example, a red light-emitting layer and a green light-emitting layer that emit red light and green light, respectively. The low-molecular material is a monomer or an oligomer having two to ten bonded monomers, and may preferably have a weight-average molecular weight of fifty thousand or less. It is to be noted that any low-molecular material whose weight-average molecular weight exceeds the above-described range is not necessarily excluded. Specific examples of the low-molecular material include a polyfluorene-based polymer derivative, a (poly)paraphenylenevinylene derivative, a polyphenylene derivative, a polyvinylcarbazole derivative, a polythiophene derivative, a perylene-based pigment, a coumarin-based pigment, a rhodamine-based pigment, or a material including any of the above-described polymer materials doped with an organic EL material. As a doping material, it is possible to use, for example, rubrene, perylene, 9,10diphenylanthracene, tetraphenylbutadiene, nile red, coumarin6, or any other equivalent material.

Further, the low-molecular material to be added to the red light-emitting layer and the green light-emitting layer refers to a material other than a compound including molecules of a high-molecular-weight polymer or condensate that is generated in such a manner that a low-molecular compound repeats an identical or similar chained reaction, and such a material is defined to have a substantially single molecular weight. Further, such a material does not make a new chemical bond among molecules as a result of heating, and exists in a monomolecular state. The weight-average molecular weight (Mw) of such a low-molecular material may be preferably fifty thousand or less. This is because a material with a smaller molecular weight to some degree has more diverse properties, and adjusts the mobility of holes or electrons, and the solubility to a bandgap or a solvent more easily, as compared with a material with a larger molecular weight having Mw exceeding fifty thousand, for example.

For such a low-molecular material, it is possible to use, for example, benzin, styryl amine, triphenylamine, porphyrin, triphenylene, azatriphenylene, tetracyanoquinodimethane, triazole, imidazole, oxadiazole, polyarylalkane, phenylenediamine, arylamine, oxazole, anthracene, fluorenone, hydrazone, stilben, or any of derivatives of those materials, or heterocyclic conjugate-based monomer or oligomer such as polysilane-based compound, vinylcarbazole-based compound, thiophene-based compound, or aniline-based compound.

Further, examples of the specific material include, but not be limited to, α-naphthylphenylphenylenediamine, porphyrin, metallic tetraphenylporphyrin, metallic naphthalocyanine, hexacyanoazatriphenylene, 7,7,8,8-tetracyanoquinodimethane (TCNQ), 7,7,8,8-tetracyano-2,3,5,6-tetrafluoroquinodimethane (F4-TCNQ), tetracyano 4,4,4-tris (3-methylphenylphenylamino) triphenylamine, N, N, N', N'-tetrakis (p-tolyl) p-phenylenediamine, N, N, N', N'-tetraphenyl-4,4'-diaminobiphenyl, N-phenylcarbazole, 4-di-p-tolylaminostilbene, poly (paraphenylenevinylene), poly (thiophenevinylene), and poly (2,2'-thienylpyrrole).

It is to be noted that, for the low-molecular material to be added to the red light-emitting layer and the green light-emitting layer, not only one kind of material but also a plurality of kinds of materials may be mixed. Further, a thickness of each of the red light-emitting layer and the green light-emitting layer may be preferably, for example, at least 10 nm but no more than 200 nm depending on a configuration of the organic EL device.

If the light-emitting layer 14 is a so-called blue light-emitting layer, such a layer is configured of, for example, a low-molecular material, and is made of at least two kinds of materials including a host material and a guest material. As the host material for configuring the blue light-emitting layer, it may be preferable to use a compound represented by Formula (1) given below.

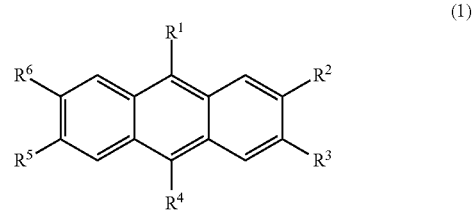

(1)

(Each of R1 to R6 is: one of a hydrogen atom, a halogen atom, a hydroxyl group, a cyano group, and a nitro group; one of a group with carbon number of 50 or less having a carbonyl group, a group with carbon number of 50 or less having a carbonyl ester group, an alkyl group with carbon number of 50 or less, an alkenyl group with carbon number of 50 or less, an alkoxyl group with carbon number of 50 or less, and derivatives thereof; or one of a group with carbon number of 30 or less having a silyl group, a group with carbon number of 30 or less having an aryl group, a group with carbon number of 30 or less having a heterocyclic group, a group with carbon number of 30 or less having an amino group, and derivatives thereof. It is to be noted that, in a case where any of the above-described substituent groups is to be used, the carbon number includes the carbon number of the substituent group to be used.)

Examples of the aryl group represented by each of R1 to R6 in Formula (1) include a phenyl group, a 1-naphtyl group, a 2-naphtyl group, a fluorenyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 1-chrysenyl group, a 6-chrysenyl group, a 2-fluoranthenyl group, a 3-fluoranthenyl group, a 2-biphenylyl group, a 3-biphenylyl group, a 4-biphenylyl group, an o-tolyl group, an m-tolyl group, a p-tolyl group, and a p-t-butylphenyl group.

Further, the group having the heterocyclic group represented by each of R1 to R6 may include a 5-membered-ring or 6-membered-ring heteroaromatic group containing oxygen atom (O), nitrogen atom (N), and sulfur atom (S) as the heteroatom, such as a condensed polycyclic heteroaromatic group with the carbon number of 2 to 20. Examples of such a heterocyclic group include a thienyl group, a fryl group, a pyrrolyl group, a pyridyl group, a quinolyl group, a quinoxalyl group, an imidazopyridyl group, and a benzothiazole group. Typical examples include a 1-pyrrolyl group, a 2-pyrrolyl group, a 3-pyrrolyl group, a pyrazinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, a 8-phenanthridinyl group, a 9-phenanthridinyl group, a 10-phenanthridinyl group, a 1-acrydinyl group, a 2-acrydinyl group, a 3-acrydinyl group, a 4-acrydinyl group, and a 9-acrydinyl group.

The group having the amino group represented by each of R1 to R6 may include any of an alkylamino group, an arylamino group, an aralkylamino group, or any other equivalent group. Preferably, any of those groups may have an aliphatic hydrocarbon group with the carbon number of 1 to 6, and/or a heteroaromatic group with the carbon number of 1 to 4. Examples of such a group include a dimethylamino group, a diethylamino group, a dibutylamino group, a diphenylamino group, a ditolylamino group, a bisbiphenylamino group, and a dinaphtylamino group. It is to be noted that any of the above-described substituent groups may form a condensed ring including two or more substituent groups, or may be a derivative thereof.

An example of the guest material includes a material with the high light-emission efficiency, that is, an organic light-emission material such as a low-molecular fluorescent material or phosphorescent pigment, or a metal complex. More specifically, it is possible to use a compound having a peak wavelength within the range of at least about 400 nm but no more than about 490 nm. As such a compound, an organic material such as a naphthalene derivative, an anthracene derivative, a naphthacene derivative, a styrylamine derivative, and a bis (azinyl) methene boron complex is used. Among all, it may be preferable to select a material from among an aminonaphthalene derivative, an aminoanthracene derivative, an aminochrysene derivative, an aminopyrene derivative, the styrylamine derivative, and the bis (azinyl) methene boron complex.

A thickness of the blue light-emitting layer 14 may be preferably, for example, at least 2 nm but no more than 50 nm depending on an overall configuration of the organic EL device 10, and may be more preferably at least 5 nm but no more than 30 nm.

The electron supply layer 15 serves to transport each of the electrons injected from the cathode 20 to the light-emitting layers 14. The electron supply layer 15 has a laminated structure, and for example, a two-layer structure in which the first layer 15A and the second layer 15B are laminated. It may be preferable that the electron supply layer 15 be greater than the hole supply layer 13 in thickness. An example of a constituent material of the first layer 15A includes a polycyclic aromatic hydrocarbon compound having a base skeleton with a 3- to 7-membered ring as a material having the orientation. Specific examples of the base skeleton of the polycyclic aromatic hydrocarbon compound include anthracene, pyrene, benzopyrene, chrysene, naphthacene, benzonaphthacene, dibenzonaphthacene, perylene, and coronene. In particular, it may be preferable to use a compound (anthracene derivative) having the anthracene represented in above Formula (1) as the base skeleton. This makes it possible to improve the efficiency of transporting electrons to the blue light-emitting layer 14.

The specific compound represented in Formula (1) above includes any of compounds represented in Formulas (1-1 to 1-109) given below.

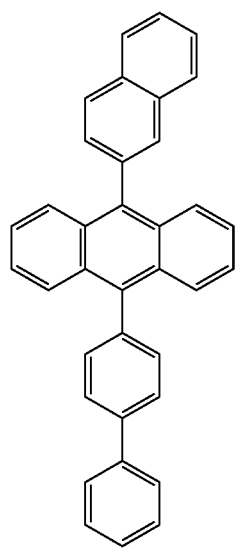

1-1

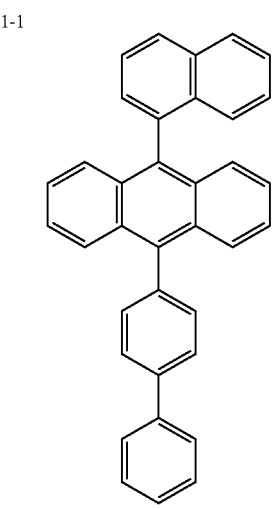

1-2

-continued
1-3
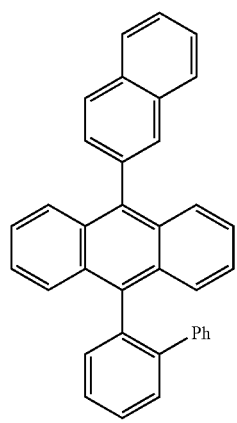
1-4
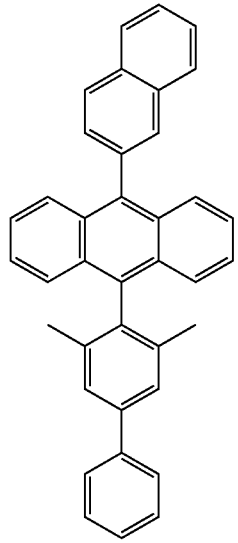
1-5
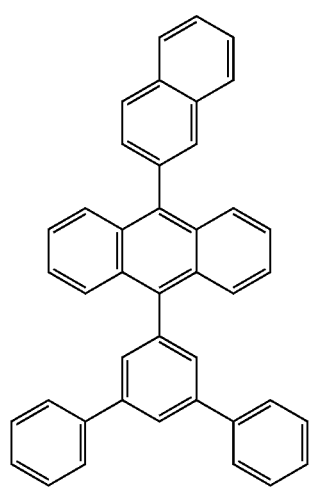
1-6
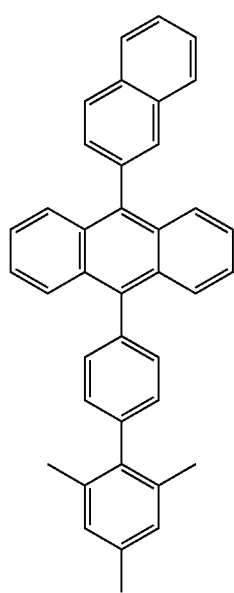

1-7
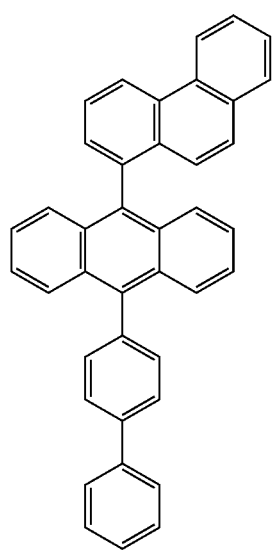
1-8
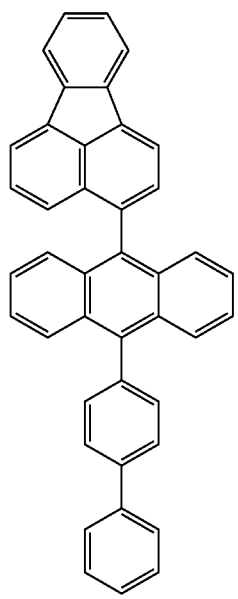
1-9
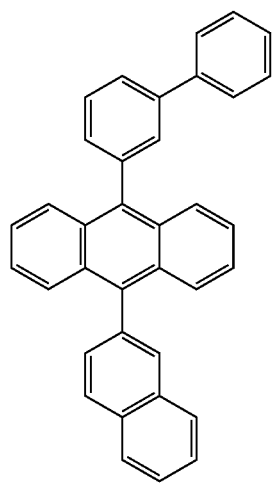
1-10
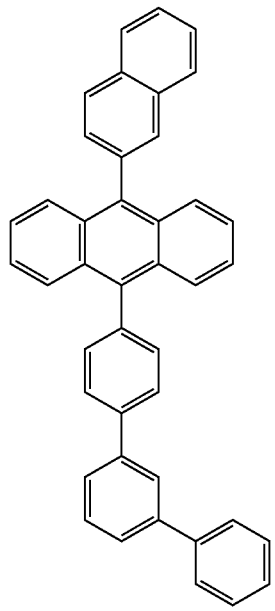

-continued
1-11
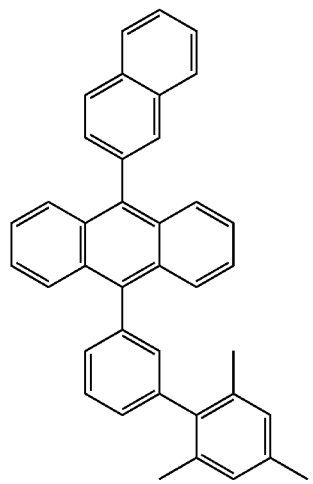
1-12
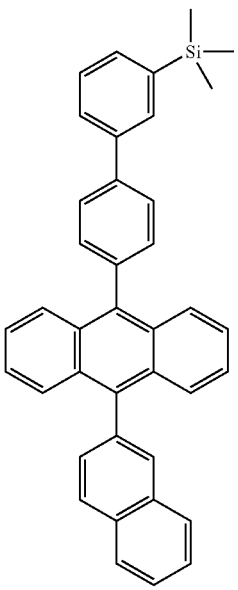
1-13
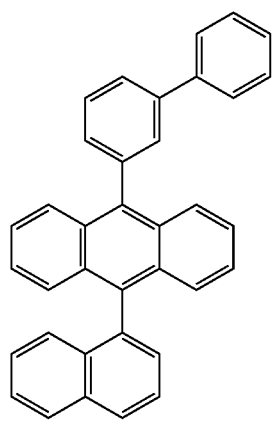
1-14
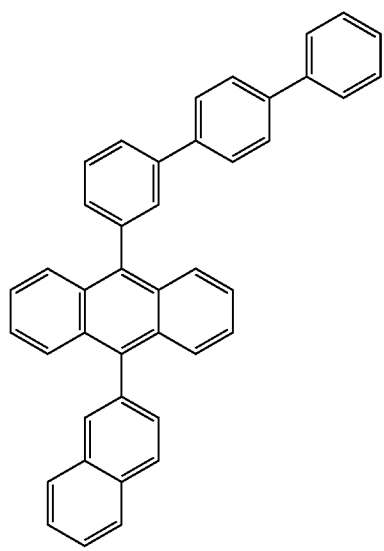

-continued
1-15
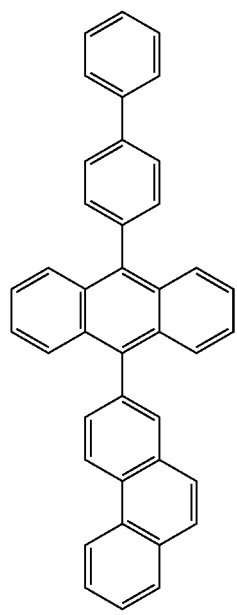
1-16
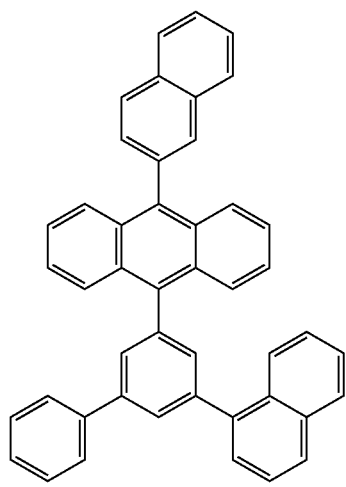
1-17
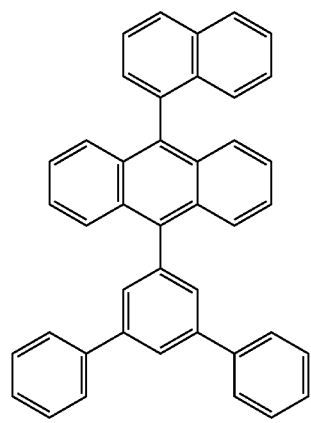
1-18
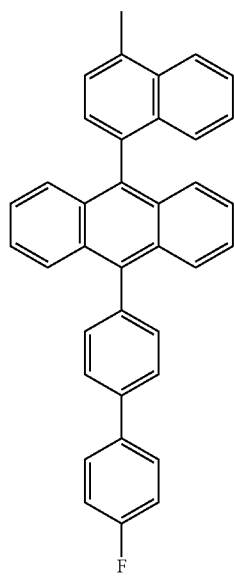

1-19
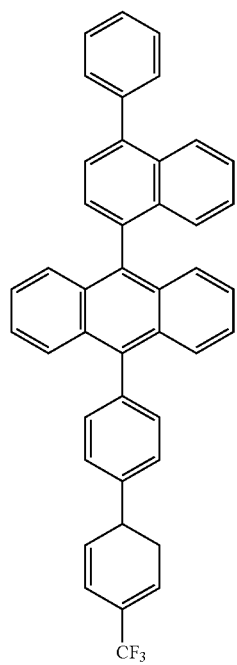
1-20
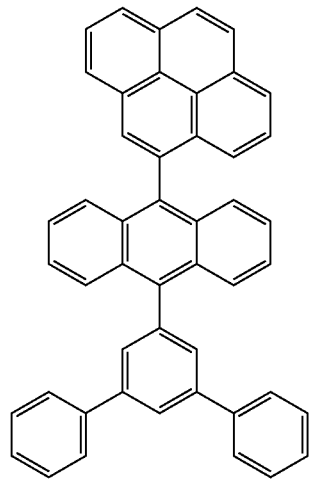
1-21
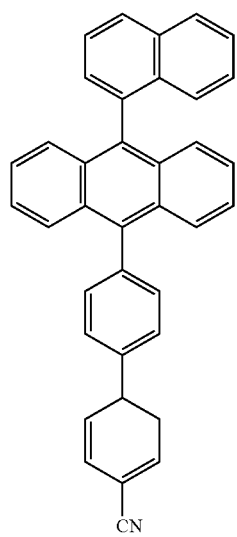
1-22
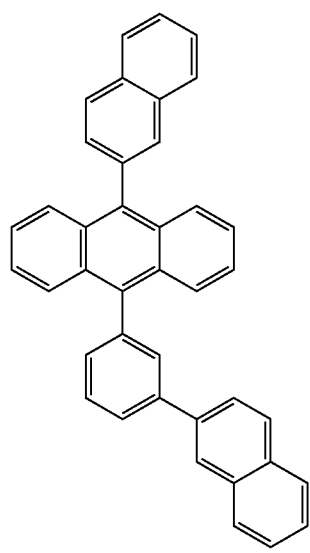

-continued
1-23
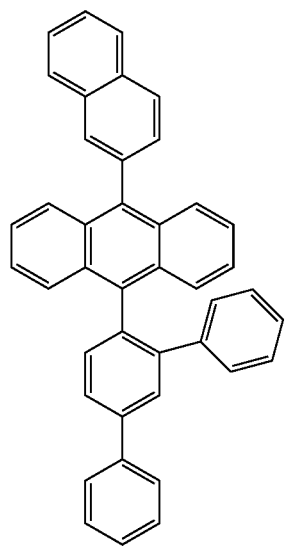
1-24
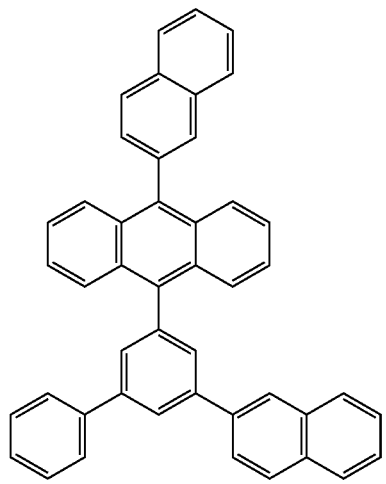
1-25
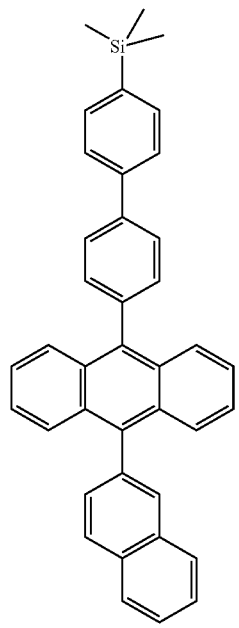
1-26
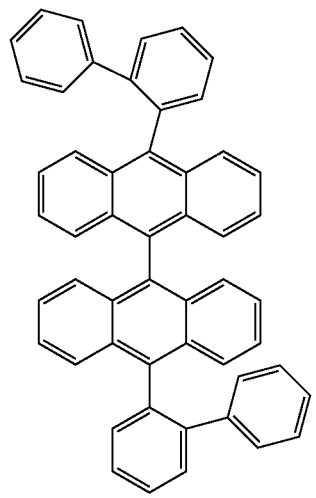
1-27
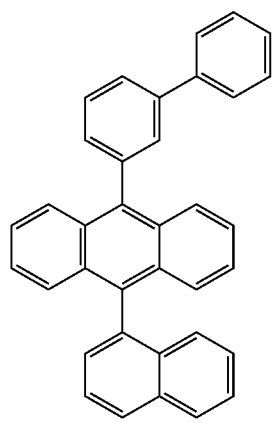
1-28
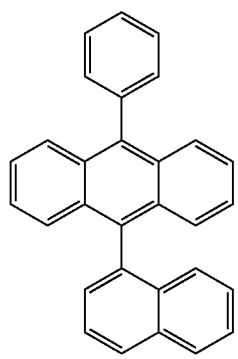

1-29
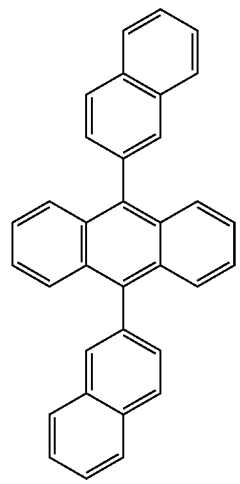
1-30
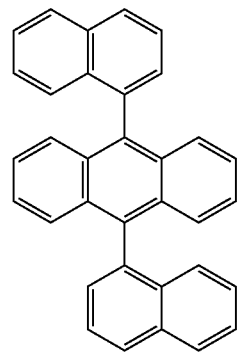
1-31
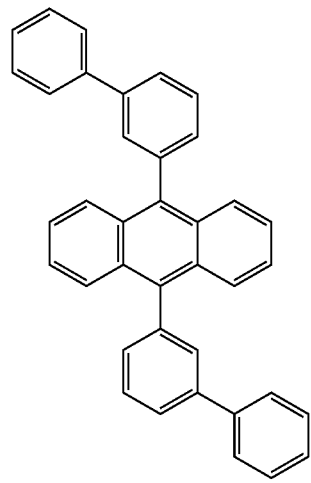
1-32
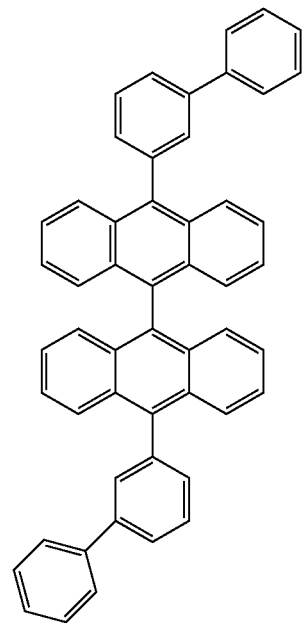

-continued
1-33
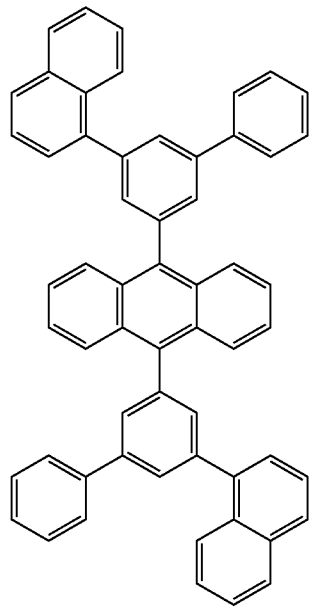
1-34
1-31
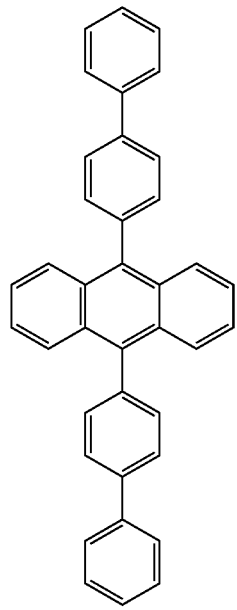
1-35
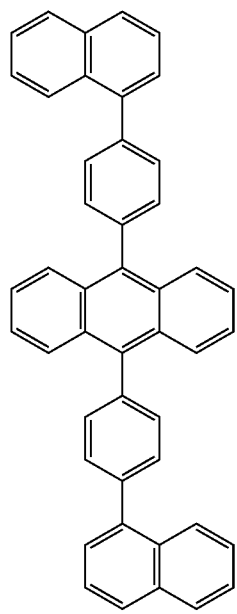
1-36
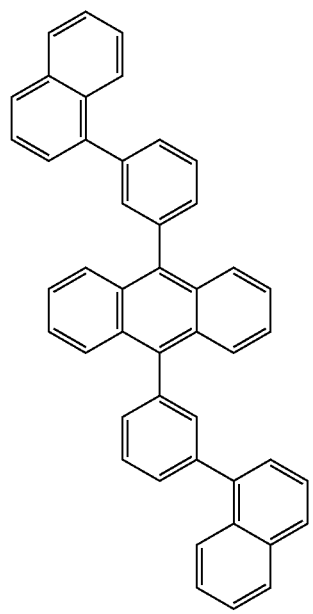
1-37
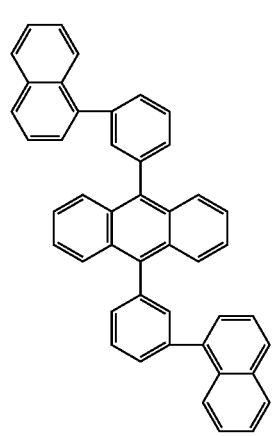
1-38
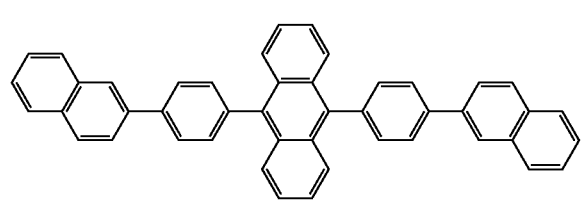

-continued
1-39
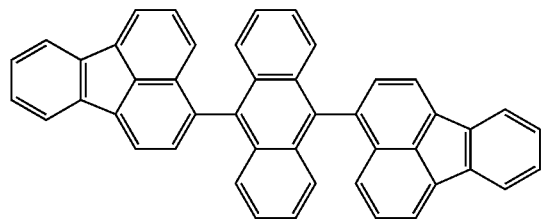
1-40
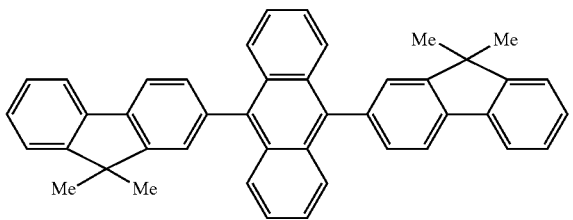
1-41
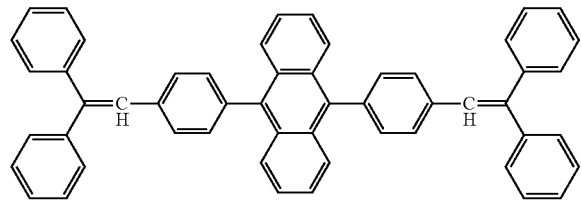
1-42
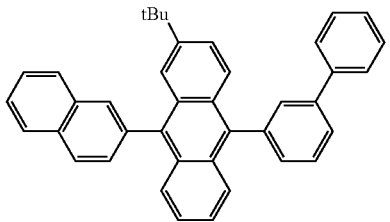
1-43
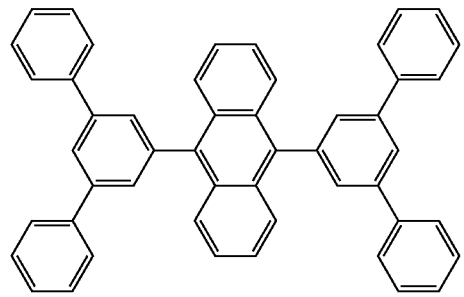
1-44
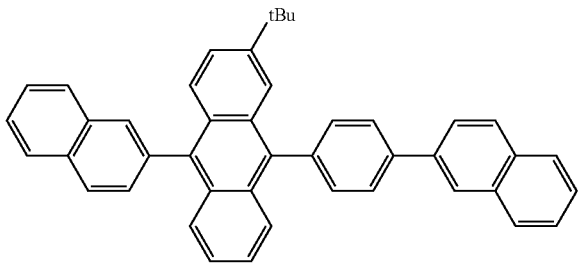
1-45
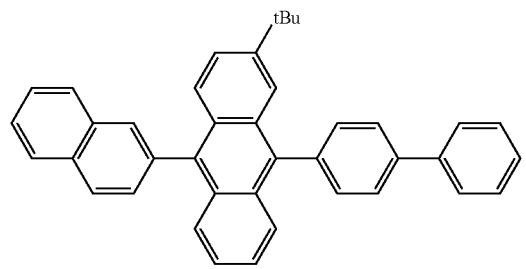
1-46
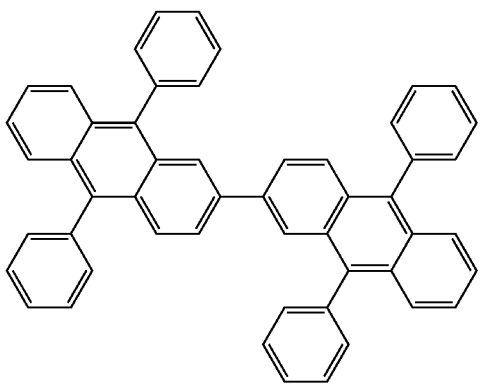

-continued
1-47
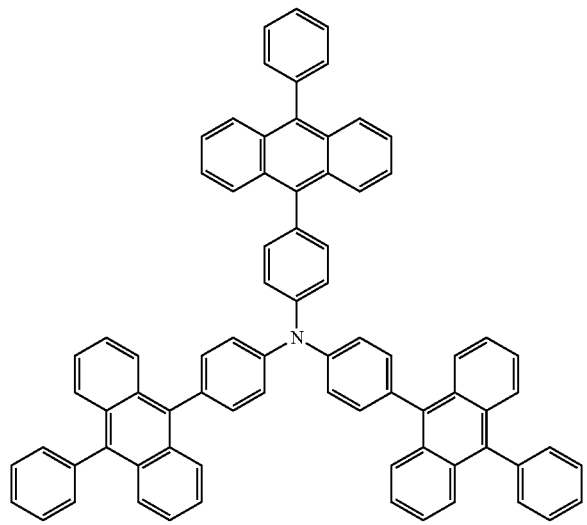
1-48
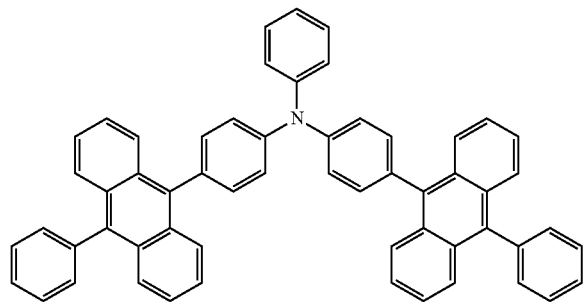
1-49
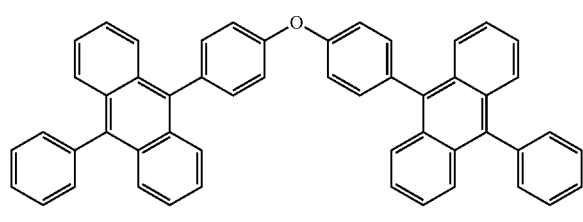
1-50
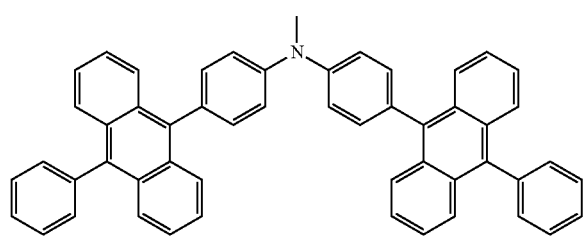
1-51
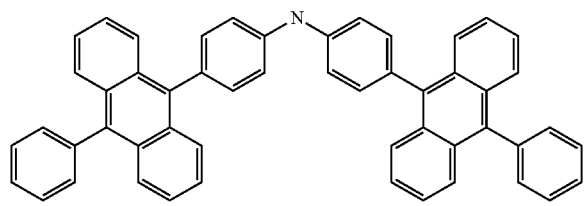
1-52
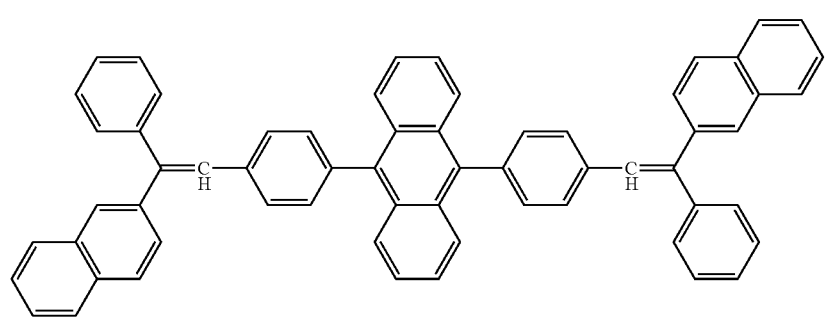
1-53
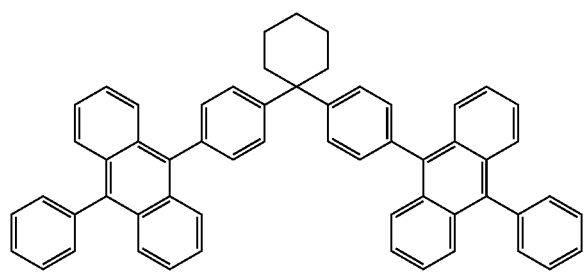
1-54
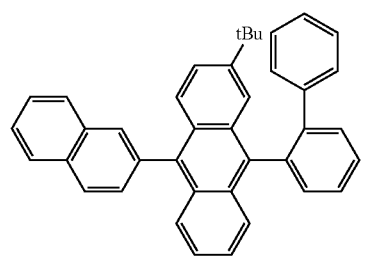

-continued
1-55
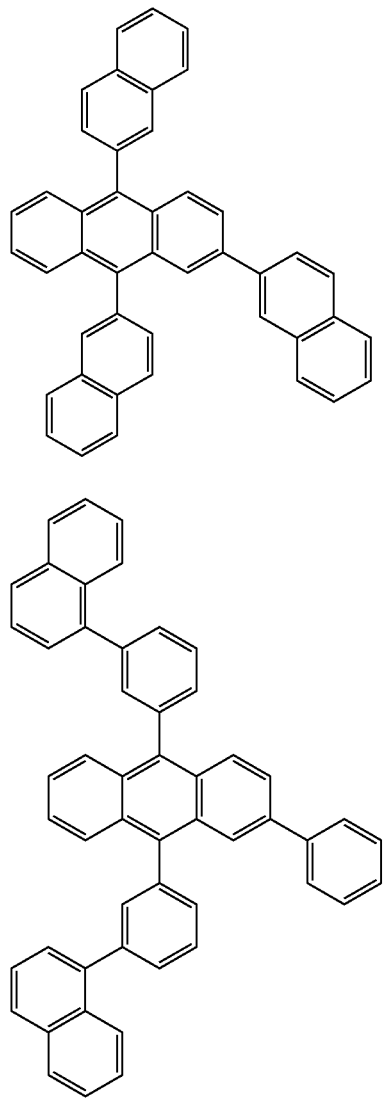
1-56
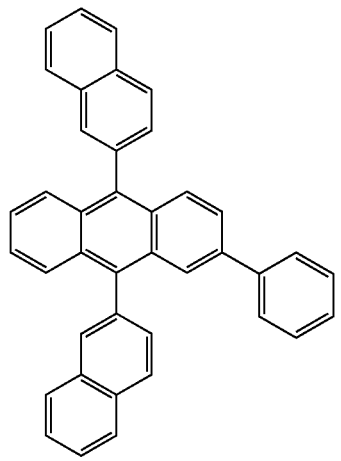
1-57
1-58
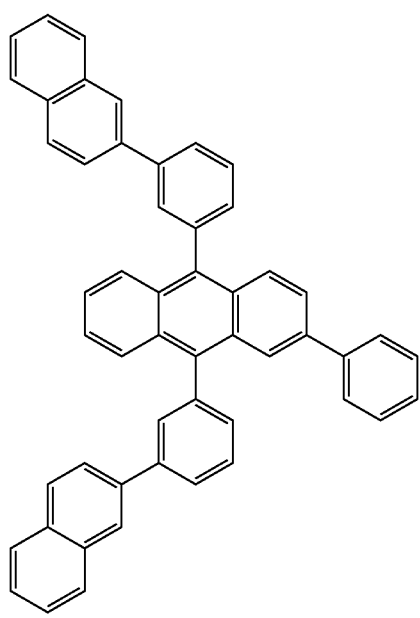
1-59
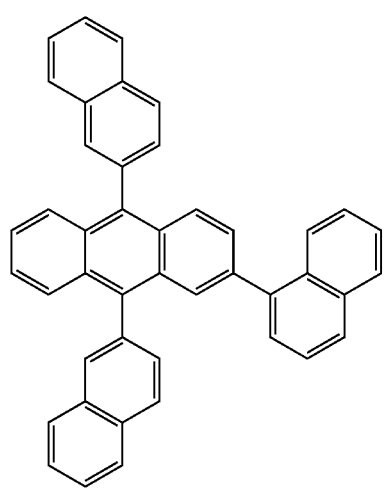
1-60
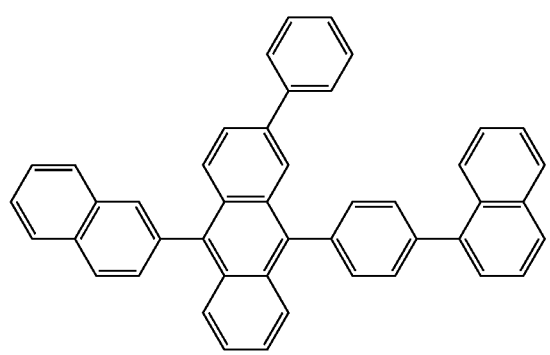

-continued
1-61
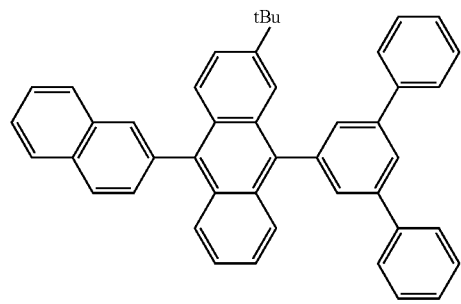
1-62
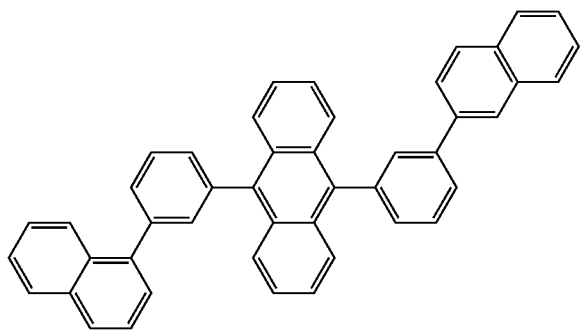
1-63
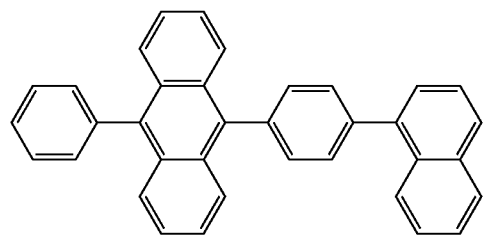
1-64
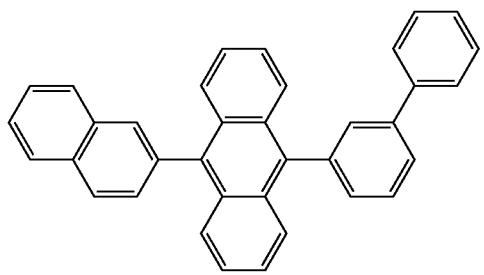
1-65
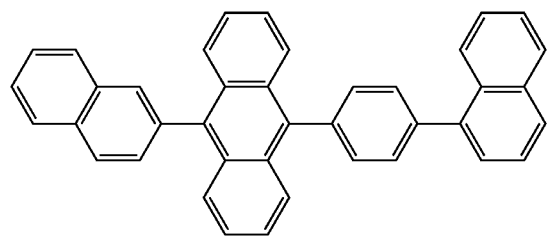
1-66
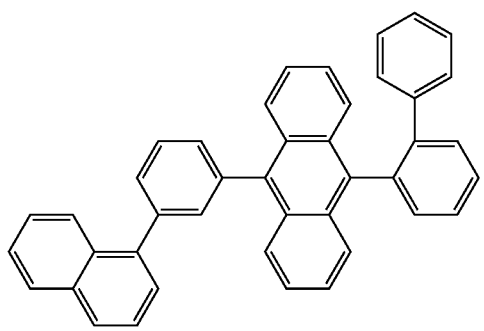
1-67
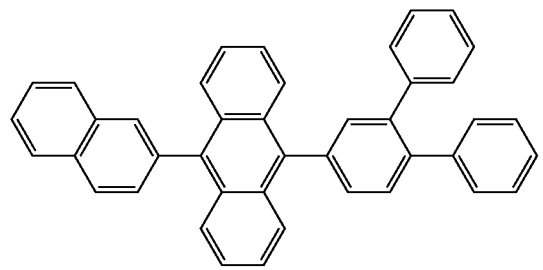
1-68
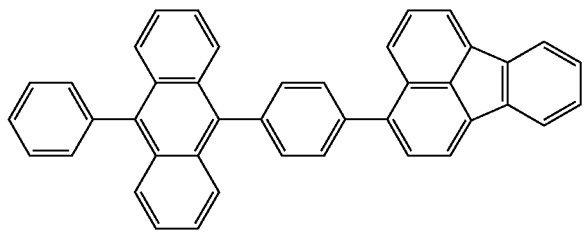
1-69
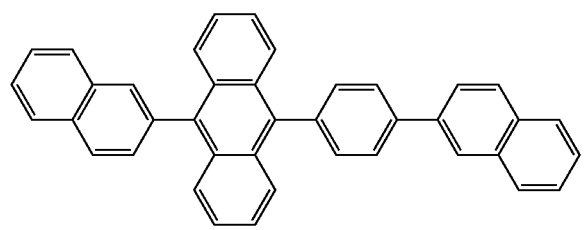
1-70
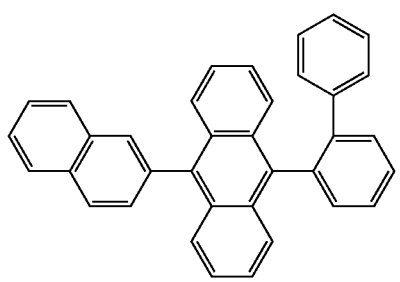

-continued
1-71
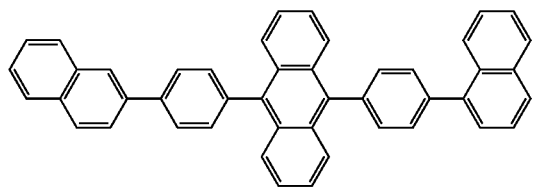
1-72
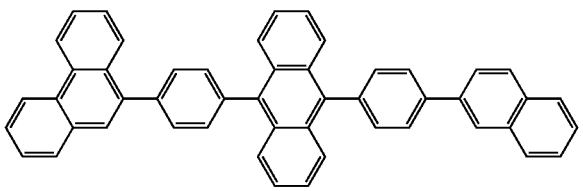
1-73
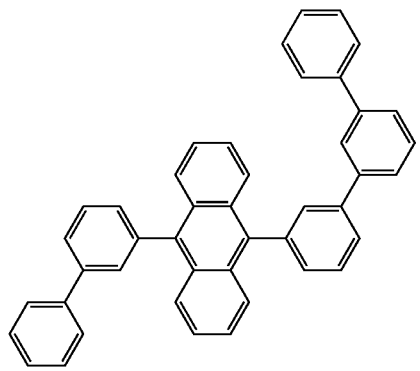
1-74
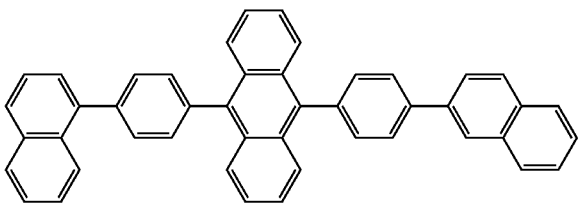
1-75
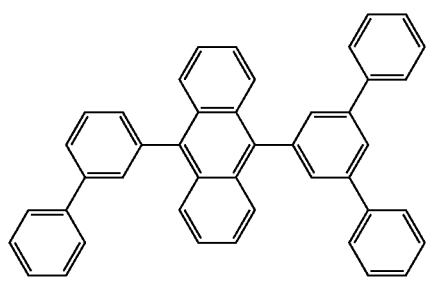
1-76
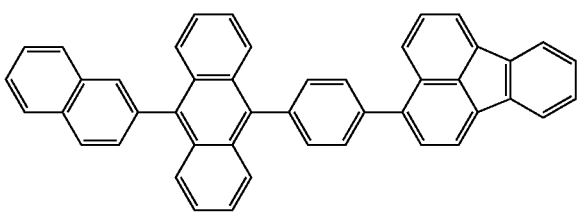
1-77
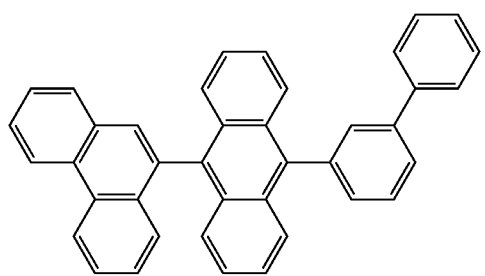
1-78
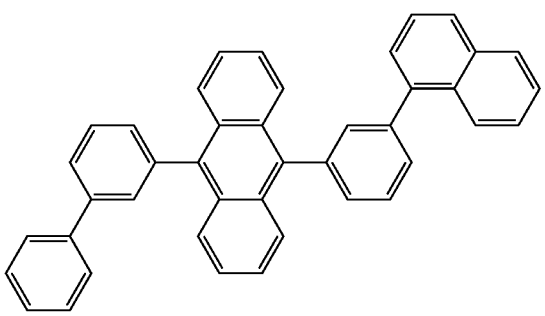
1-79
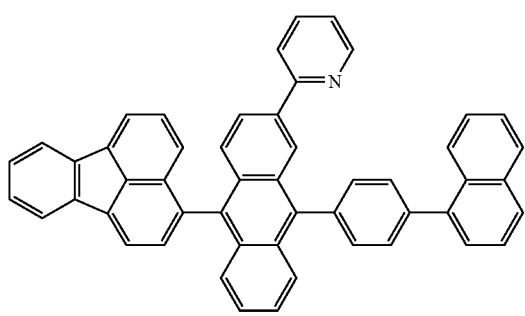
1-80
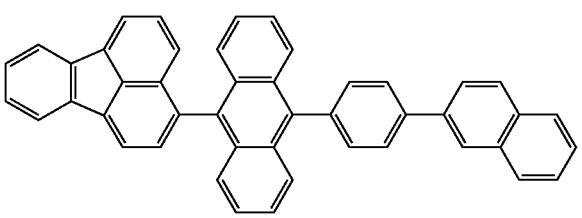

-continued
1-81
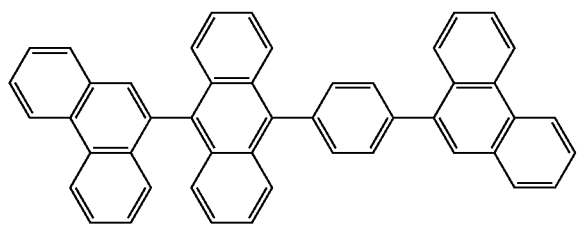
1-82
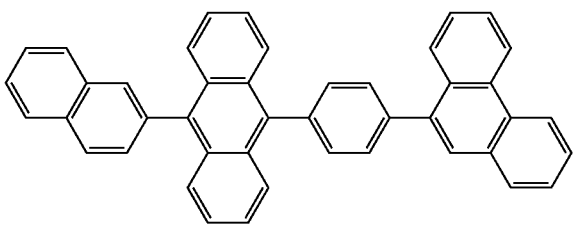
1-83
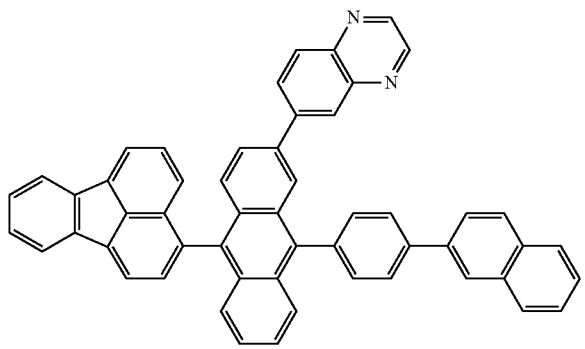
1-84
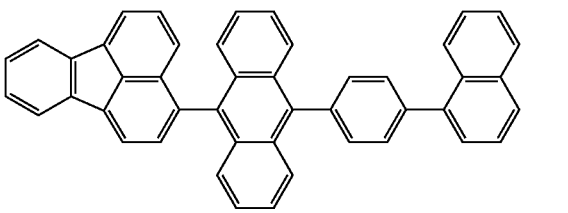
1-85
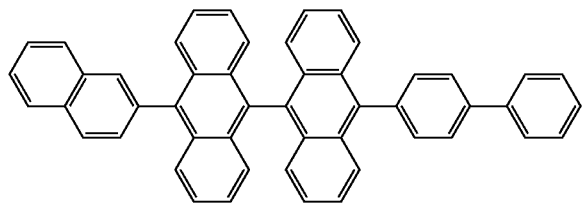
1-86
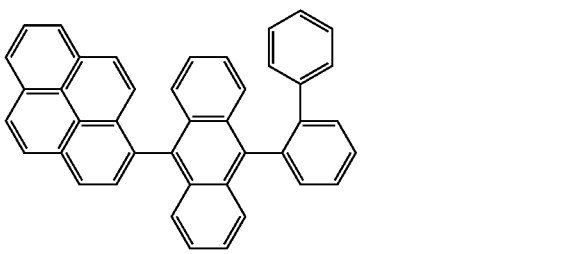
1-87
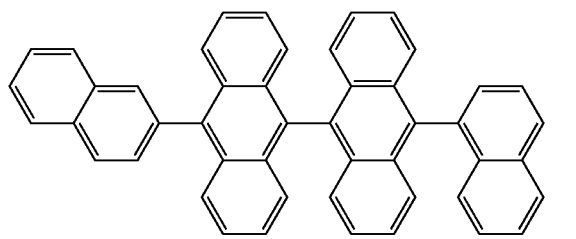
1-88
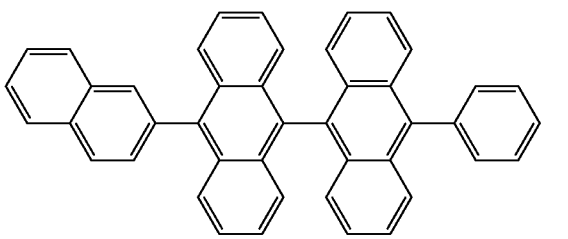
1-89
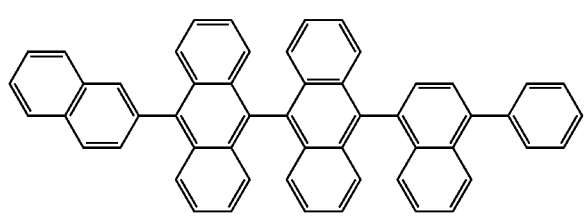
1-90
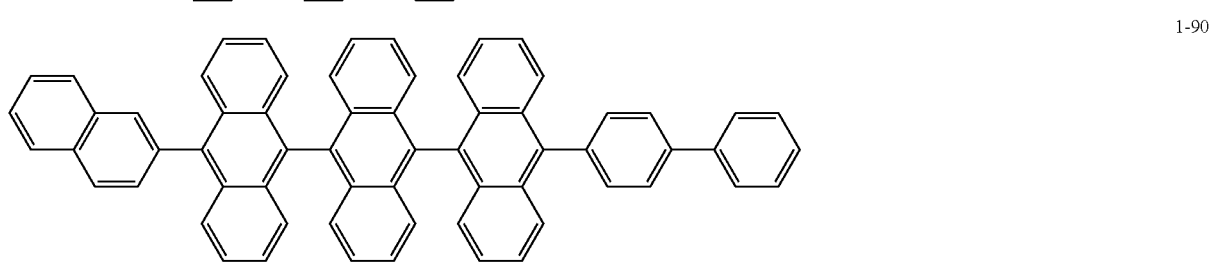

-continued
1-91
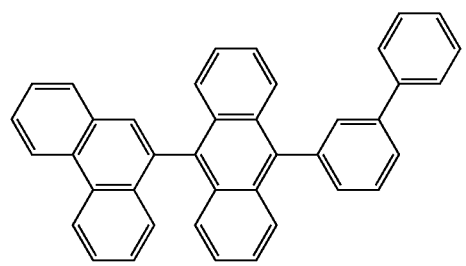
1-92
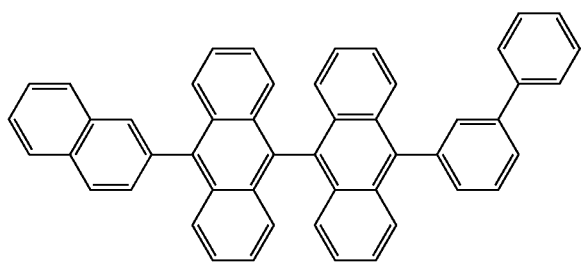
1-93
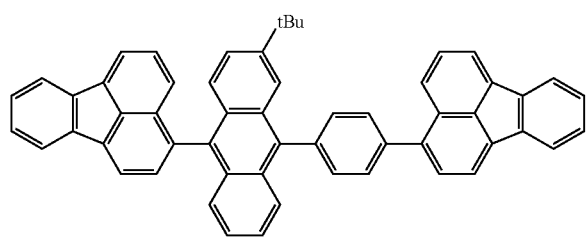
1-94
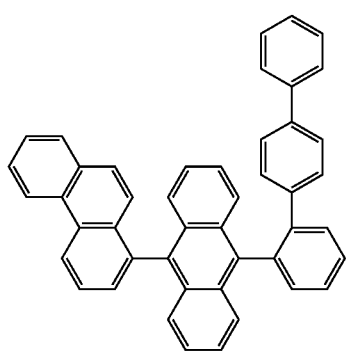
1-95
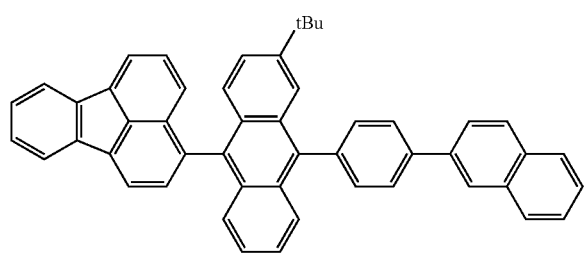
1-96
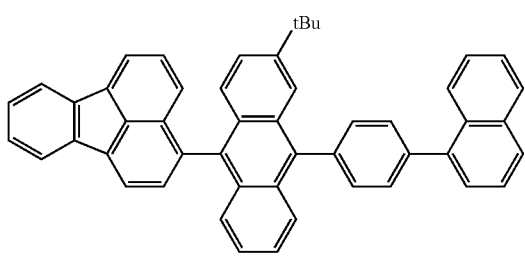
1-97
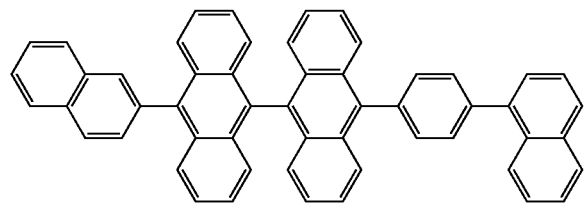
1-98
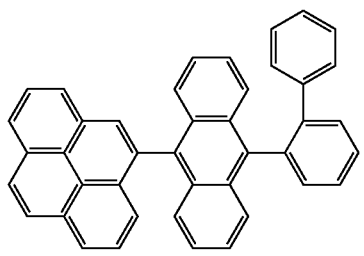
1-99
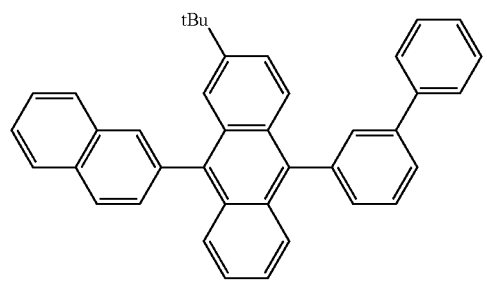
1-100
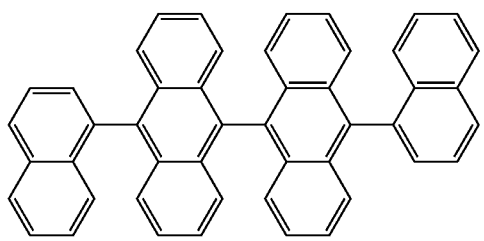

-continued
1-101
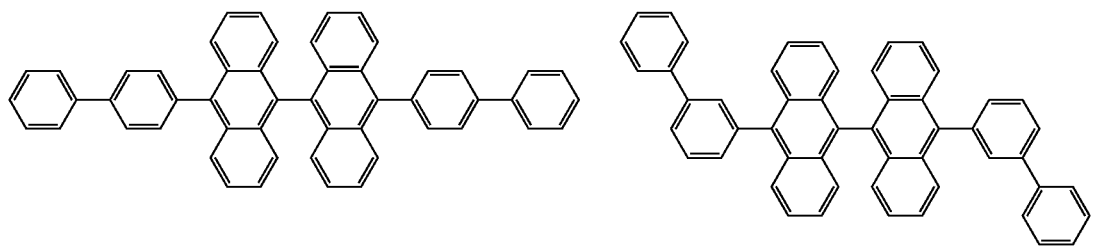
1-102
1-103
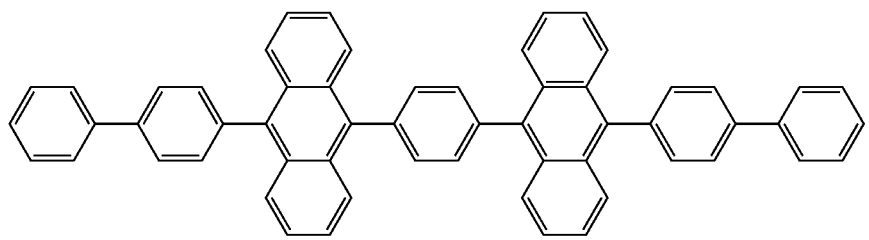
1-104
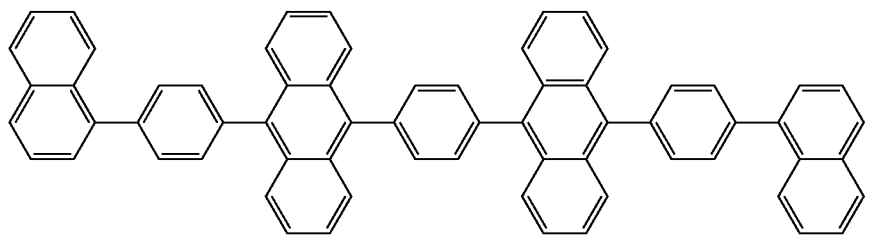
1-105
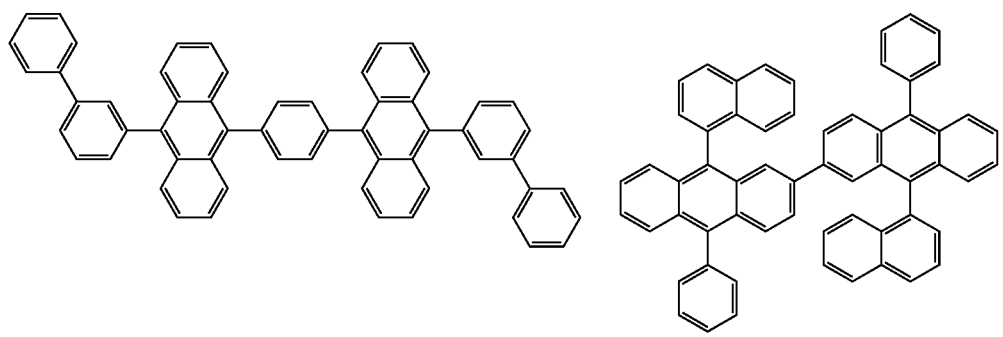
1-106
1-107
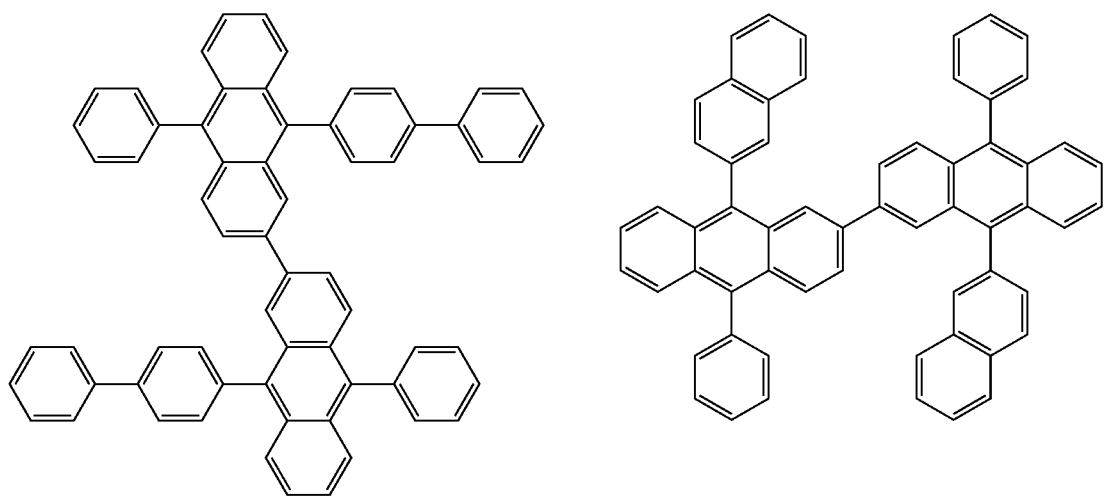
1-108

1-109

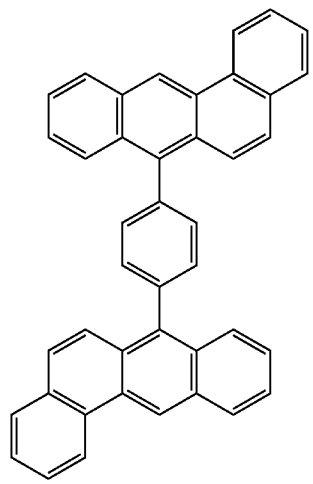

1-110

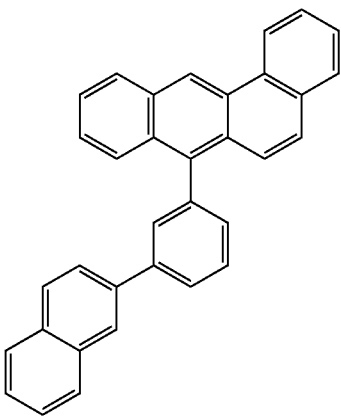

1-111

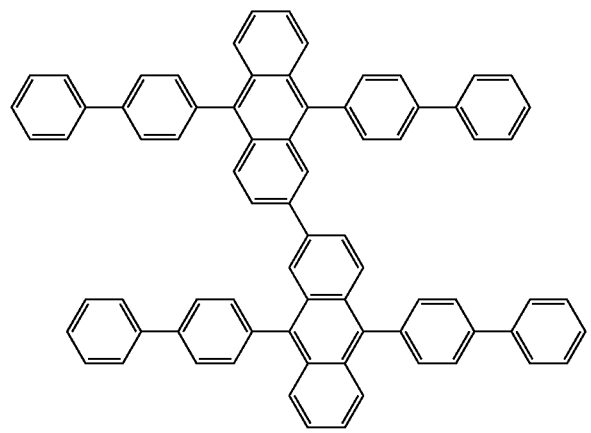

For the second layer 15B, it may be preferable to use a material having the superior electron transport capability and the high property of contacting with the cathode 20, and such a material may have preferably the orientation that is lower than that of a constituent material of the first layer 15A. Further, such a material may be preferably a material containing a larger amount of nitrogen element, and for example, it may be preferable to use a nitrogen-containing heterocyclic compound. This improves the efficiency of injecting the electrons from the cathode 20. As a specific material of the second layer 15B, it may be preferable to use a phenanthroline derivative having one or more of an imidazole derivative represented by Formula (2) given below and a phenanthroline ring represented by Formula (3) given below.

hydrocarbon group with carbon number of 6 to 60, a nitrogen-containing heterocyclic group with carbon number of 6 to 60, an alkoxyl group with carbon number of 1 to 20, and derivatives thereof. n is an integer in a range of 0 to 4, and m is an integer in a range of 0 to 2. B is one of an arylene group with carbon number of 60 or less, a pyridynylene group with carbon number of 60 or less, a quinolynylene group with carbon number of 60 or less, a fluorenylene group with carbon number of 60 or less, and derivatives thereof. Ar is one of an alkyl group with carbon number of 1 to 20, an alkoxyl group with carbon number of 1 to 20, an aromatic hydrocarbon group with carbon number of 6 to 60, a heterocyclic group with carbon number of 3 to 60, and derivatives thereof.)

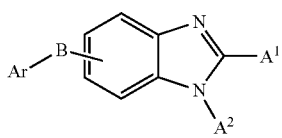

(2)

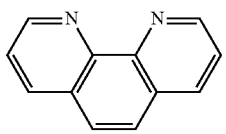

(3)

(A1 and A2 are independent from each other, and each of them is: one of a hydrogen atom and a halogen atom; or one of an alkyl group with carbon number of 1 to 20, an aromatic Specific examples of the imidazole derivative represented by Formula (2) include any of compounds represented in Formulas (2-1 to 2-48) given below.

|     | Ar (α) | B | Ar | |
| --- | --- | --- | --- | --- |
|     |        |   | Ar (1) | AR (2) |
| 2-1 | 6-methylbenzimidazole with 2-phenyl and N-(2-pyridyl) | p-phenylene | 9,10-anthracenyl | 2-naphthyl |
| 2-2 | 5-methylbenzimidazole with 2-phenyl and N-(2-pyridyl) | p-phenylene | 9,10-anthracenyl | 2-naphthyl |
| 2-3 | methyl-triazolopyridine with phenyl and N-(3-pyridyl) | p-phenylene | 9,10-anthracenyl | 2-naphthyl |
| 2-4 | 7-methylbenzimidazole with 2-phenyl and N-(3-pyridyl) | p-phenylene | 9,10-anthracenyl | 2-naphthyl |
| 2-5 | 6-methyl-2-methylbenzimidazole N-phenyl | p-phenylene | 9,10-anthracenyl | 2-naphthyl |
| 2-6 | 5-methyl-2-phenyl-N-methylbenzimidazole | p-phenylene | 9,10-anthracenyl | 2-naphthyl |

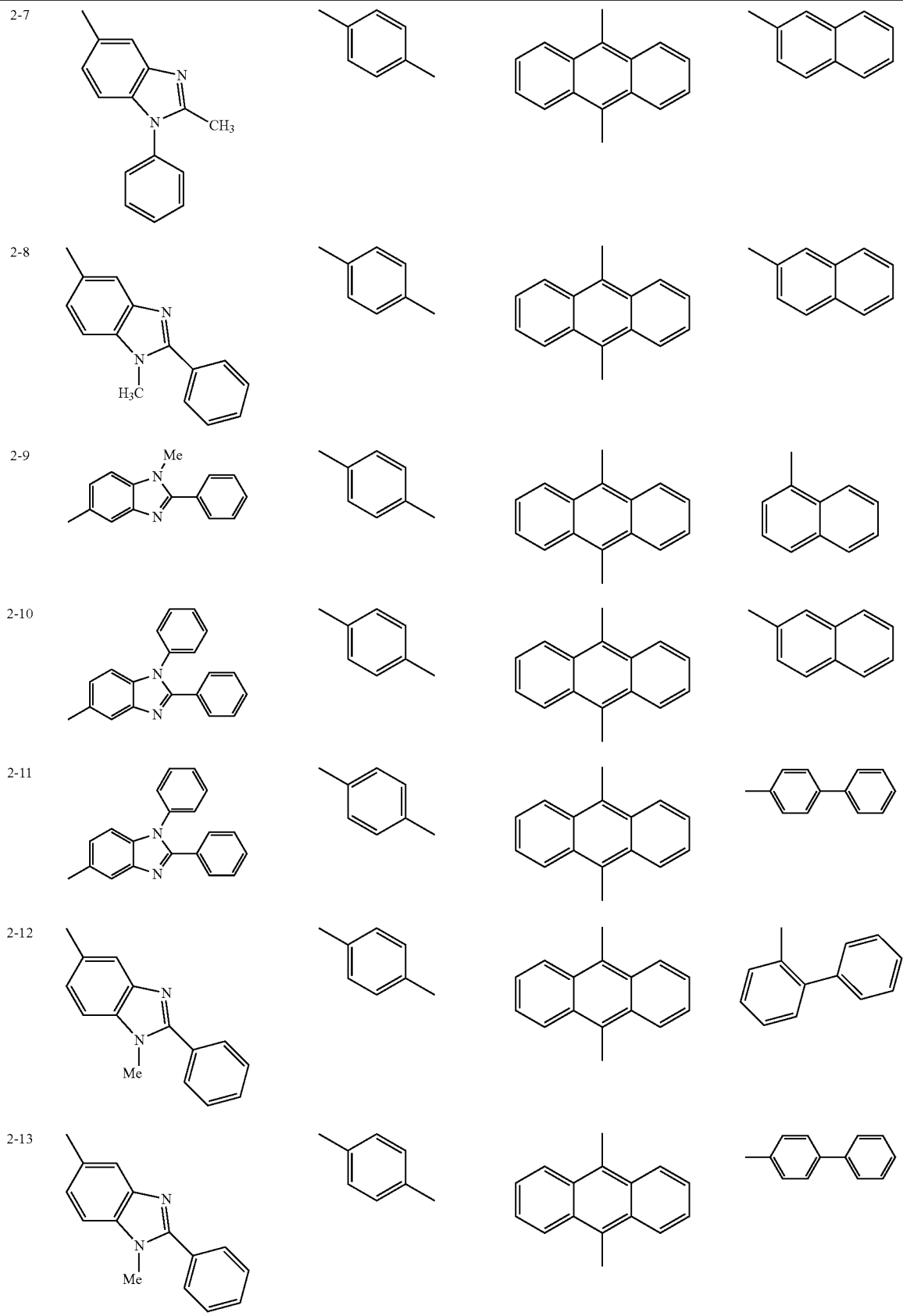

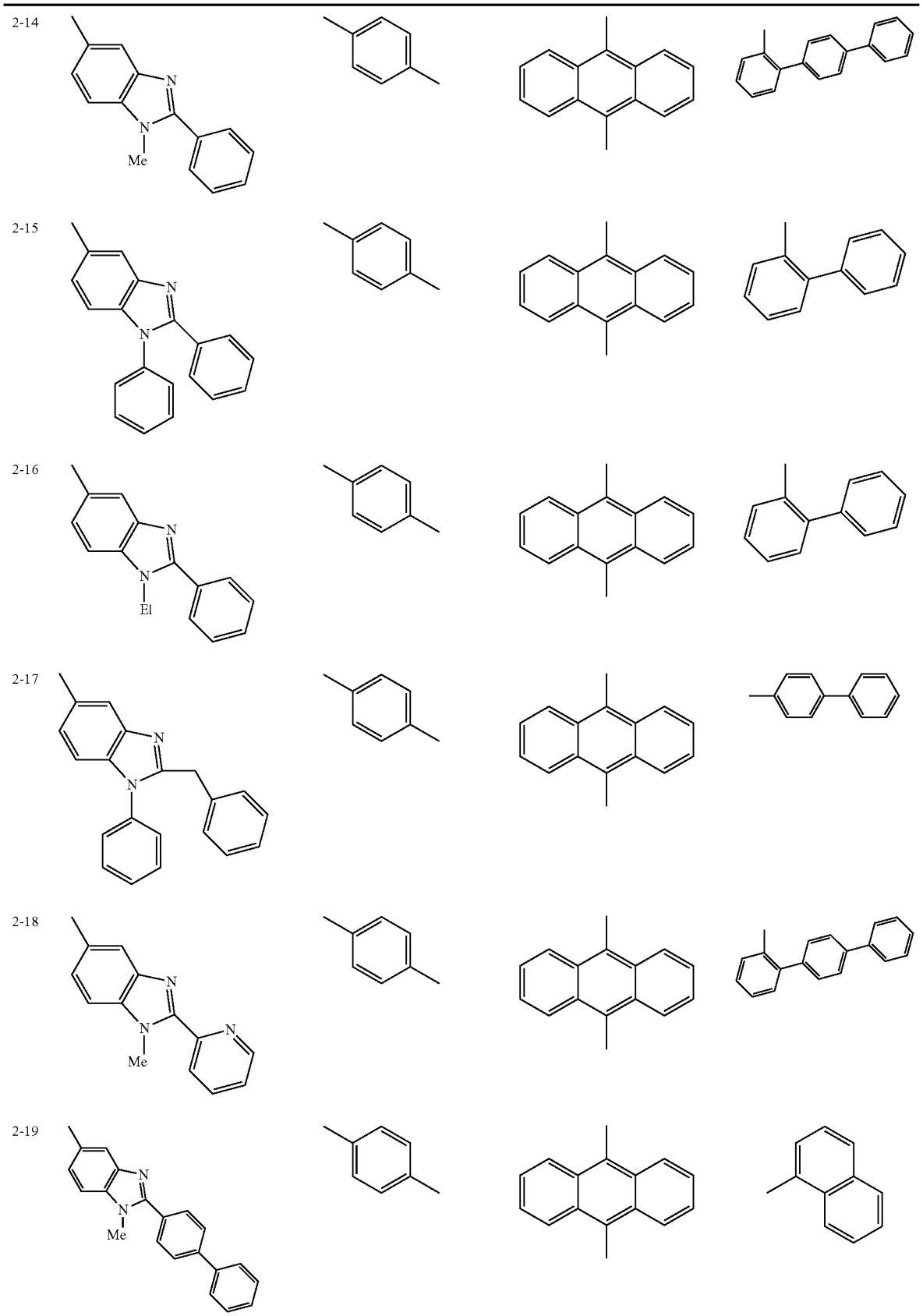

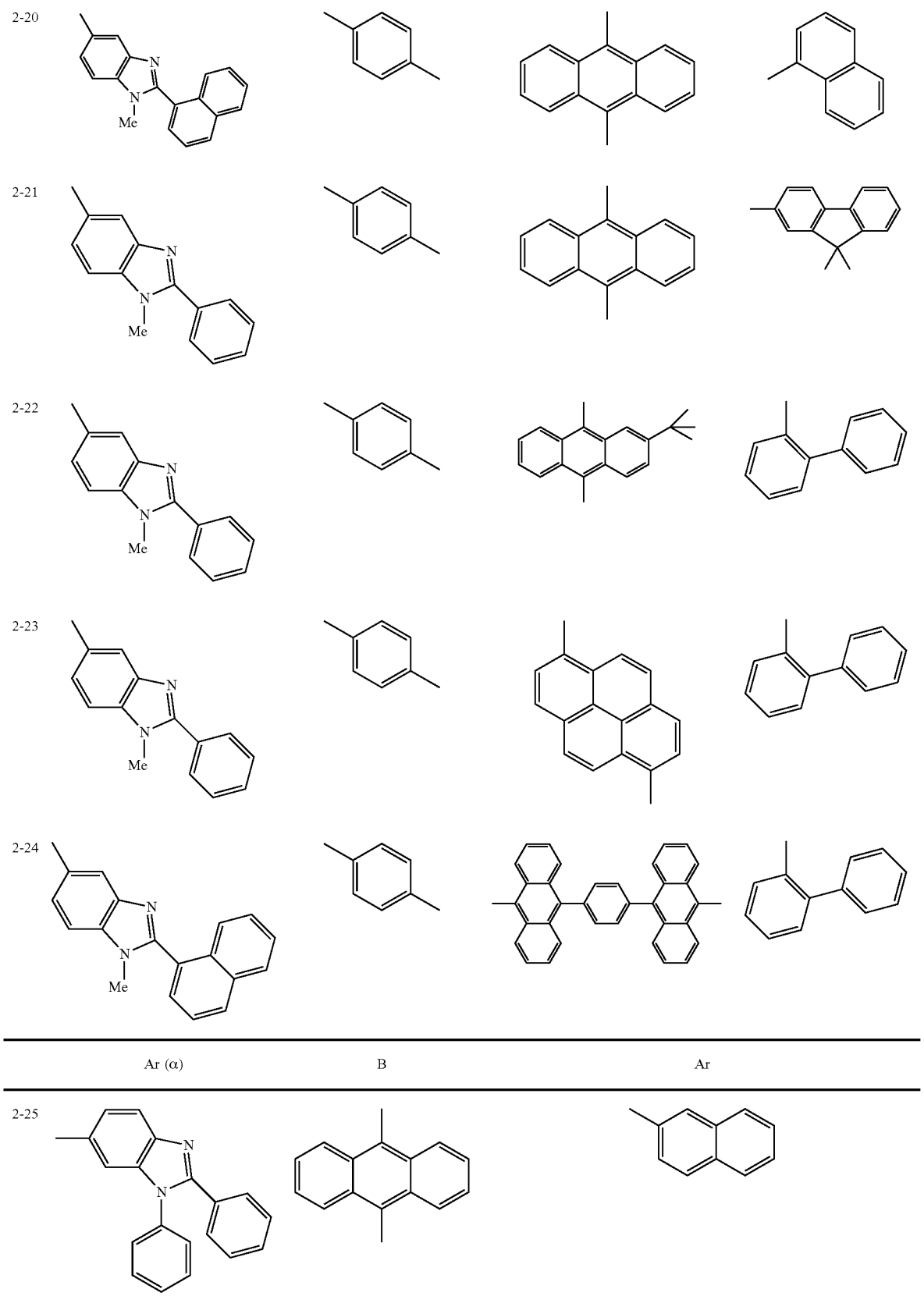

-continued
| | | | |
|---|---|---|---|
| 2-26 | 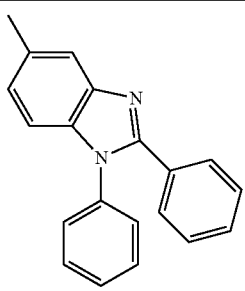 | 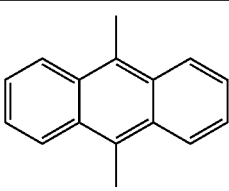 | 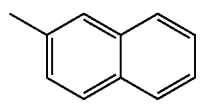 |
| 2-27 | 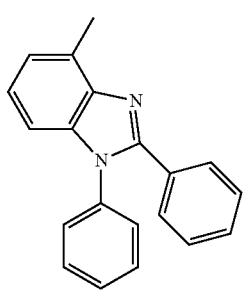 [SMILES: Cc1cccc2c1nc(-c1ccccc1)n2-c1ccccc1] | 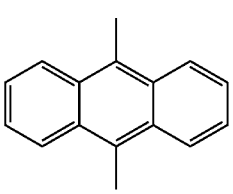 [SMILES: Cc1c2ccccc2c(C)c2ccccc12] | 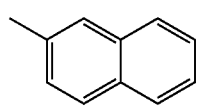 |
| 2-28 | 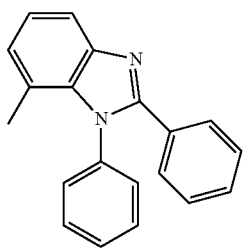 [SMILES: Cc1cccc2nc(-c3ccccc3)n(-c3ccccc3)c12] | 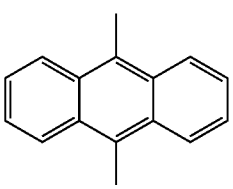 [SMILES: Cc1c2ccccc2c(C)c2ccccc12] | 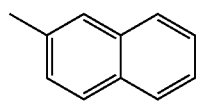 |
| 2-29 | 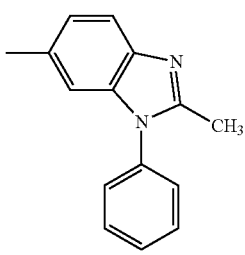 | 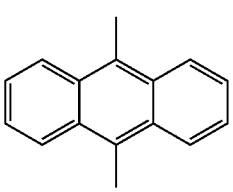 [SMILES: Cc1c2ccccc2c(C)c2ccccc12] | 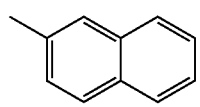 |
| 2-30 | 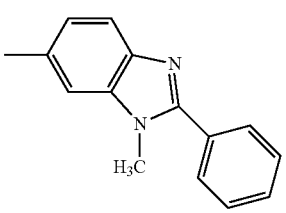 [SMILES: Cc1ccc2nc(-c3ccccc3)n(C)c2c1] | 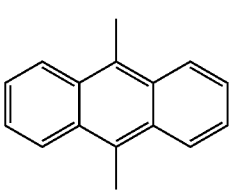 [SMILES: Cc1c2ccccc2c(C)c2ccccc12] | 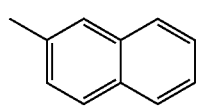 |
| 2-31 | 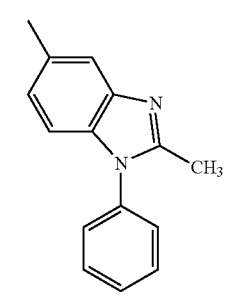 [SMILES: Cc1ccc2c(c1)nc(C)n2-c1ccccc1] | 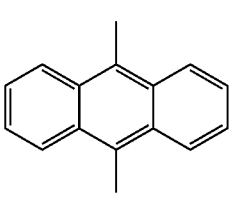 [SMILES: Cc1c2ccccc2c(C)c2ccccc12] | 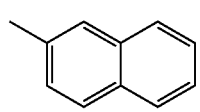 |

2-32 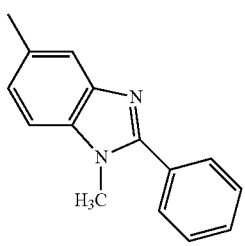 [SMILES: Cc1ccc2c(c1)nc(-c1ccccc1)n2C] 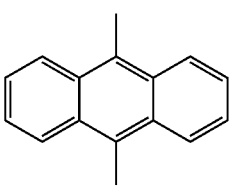 [SMILES: Cc1c2ccccc2c(C)c2ccccc12] 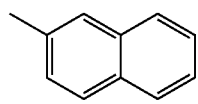
2-33 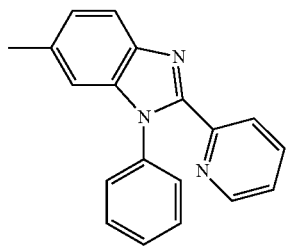 [SMILES: Cc1ccc2nc(-c3ccccn3)n(-c3ccccc3)c2c1] 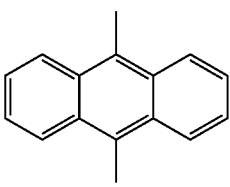 [SMILES: Cc1c2ccccc2c(C)c2ccccc12] 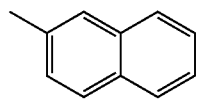
2-34 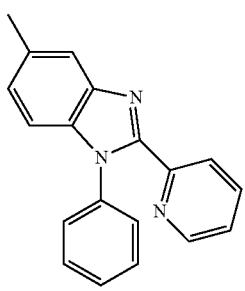 [SMILES: Cc1ccc2c(c1)nc(-c1ccccn1)n2-c1ccccc1] 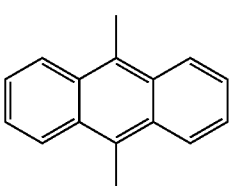 [SMILES: Cc1c2ccccc2c(C)c2ccccc12] 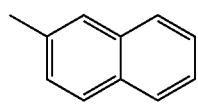
2-35 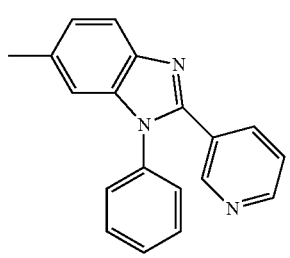 [SMILES: Cc1ccc2nc(-c3cccnc3)n(-c3ccccc3)c2c1] 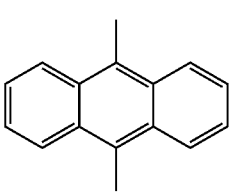 [SMILES: Cc1c2ccccc2c(C)c2ccccc12] 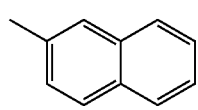
2-36 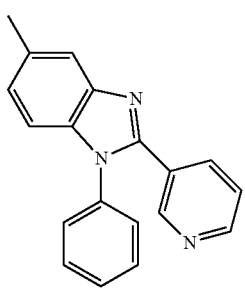 [SMILES: Cc1ccc2c(c1)nc(-c1cccnc1)n2-c1ccccc1] 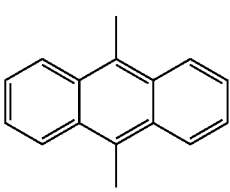 [SMILES: Cc1c2ccccc2c(C)c2ccccc12] 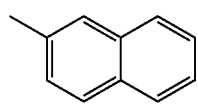
2-37 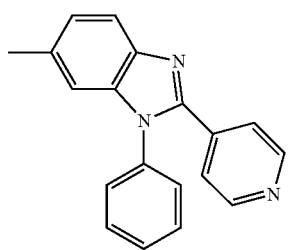 [SMILES: Cc1ccc2nc(-c3ccncc3)n(-c3ccccc3)c2c1] 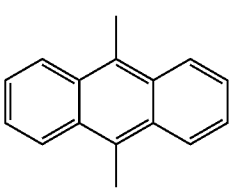 [SMILES: Cc1c2ccccc2c(C)c2ccccc12] 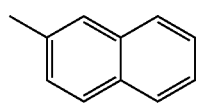

| | | | |
|---|---|---|---|
| 2-38 | 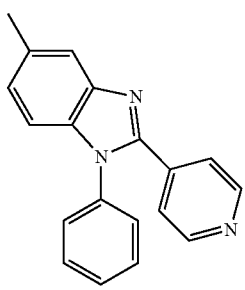 [SMILES: Cc1ccc2c(c1)nc(-c1ccncc1)n2-c1ccccc1] | 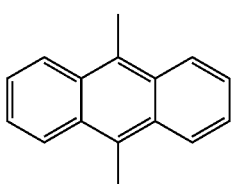 [SMILES: Cc1c2ccccc2c(C)c2ccccc12] | 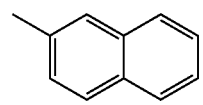 |
| 2-39 | 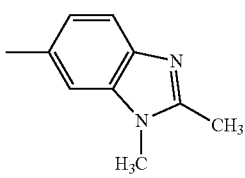 | 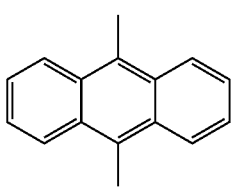 [SMILES: Cc1c2ccccc2c(C)c2ccccc12] | 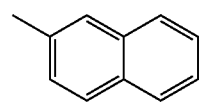 |
| 2-40 | 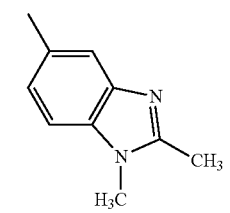 | 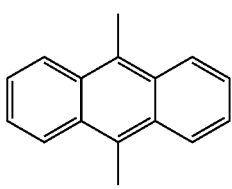 [SMILES: Cc1c2ccccc2c(C)c2ccccc12] | 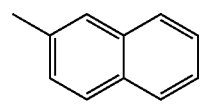 |
| 2-41 | 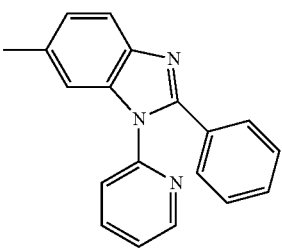 [SMILES: Cc1ccc2nc(-c3ccccc3)n(-c3ccccn3)c2c1] | 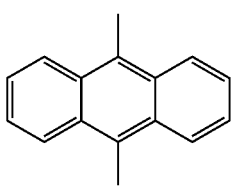 [SMILES: Cc1c2ccccc2c(C)c2ccccc12] | 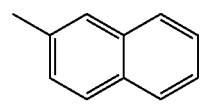 |
| 2-42 | 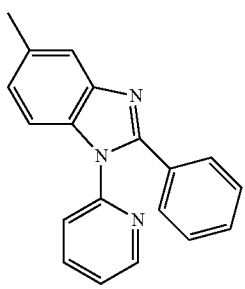 [SMILES: Cc1ccc2c(c1)nc(-c1ccccc1)n2-c1ccccn1] | 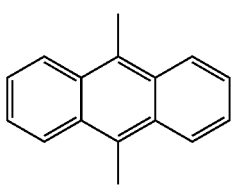 [SMILES: Cc1c2ccccc2c(C)c2ccccc12] | 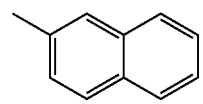 |
| 2-43 | 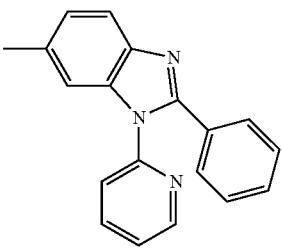 [SMILES: Cc1ccc2nc(-c3ccccc3)n(-c3ccccn3)c2c1] | 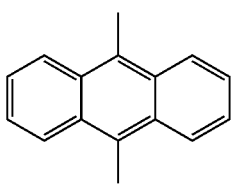 [SMILES: Cc1c2ccccc2c(C)c2ccccc12] | 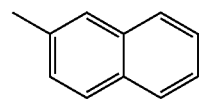 |

| | | | |
|---|---|---|---|
| 2-44 | 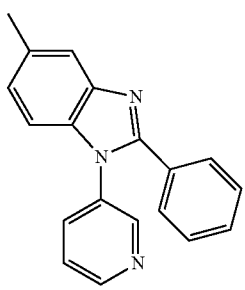 [SMILES: Cc1ccc2c(c1)nc(-c1ccccc1)n2-c1cccnc1] | 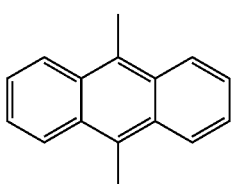 [SMILES: Cc1c2ccccc2c(C)c2ccccc12] | 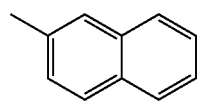 |
| 2-45 | 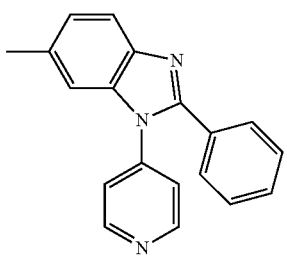 [SMILES: Cc1ccc2nc(-c3ccccc3)n(-c3ccncc3)c2c1] | 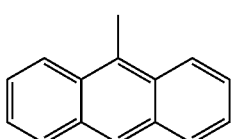 | 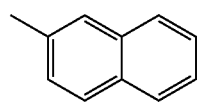 |
| 2-46 | 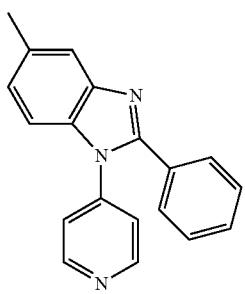 [SMILES: Cc1ccc2c(c1)nc(-c1ccccc1)n2-c1ccncc1] | 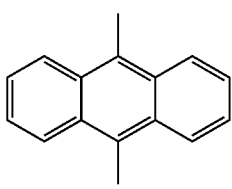 [SMILES: Cc1c2ccccc2c(C)c2ccccc12] | 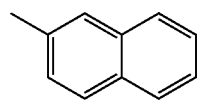 |
| 2-47 | 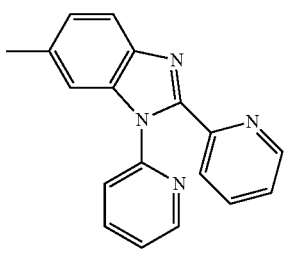 [SMILES: Cc1ccc2nc(-c3ccccn3)n(-c3ccccn3)c2c1] | 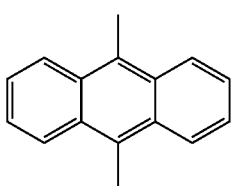 [SMILES: Cc1c2ccccc2c(C)c2ccccc12] | 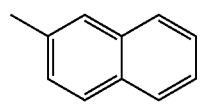 |
| 2-48 | 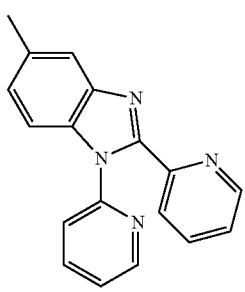 [SMILES: Cc1ccc2c(c1)nc(-c1ccccn1)n2-c1ccccn1] | 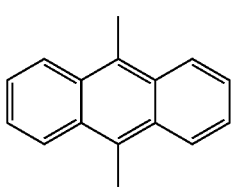 [SMILES: Cc1c2ccccc2c(C)c2ccccc12] | 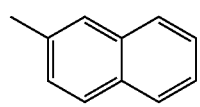 |

Other than the above-mentioned materials, any of compounds represented in Formulas (2-49 to 2-60) given below may be used.
2-49
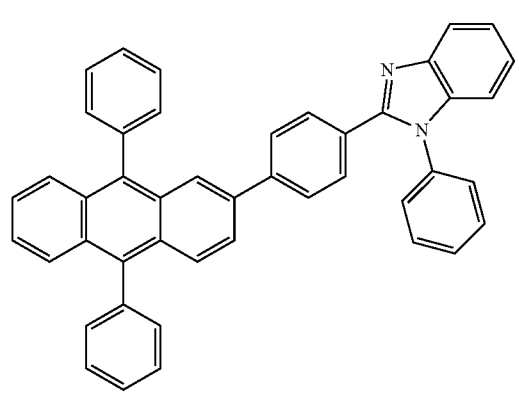
2-50
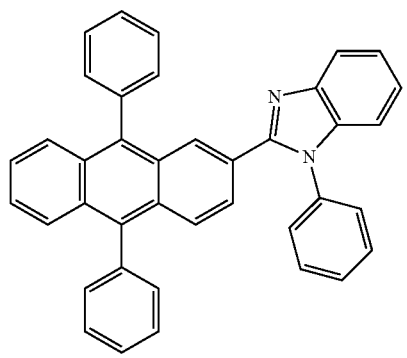
2-51
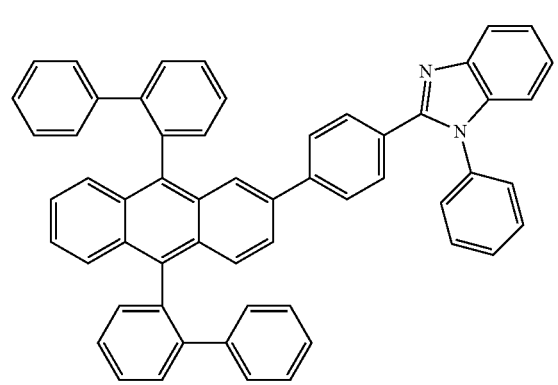
2-52
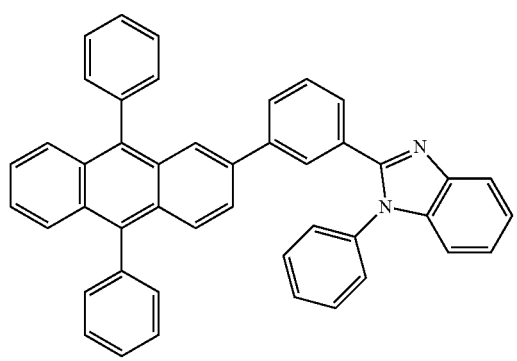
2-53
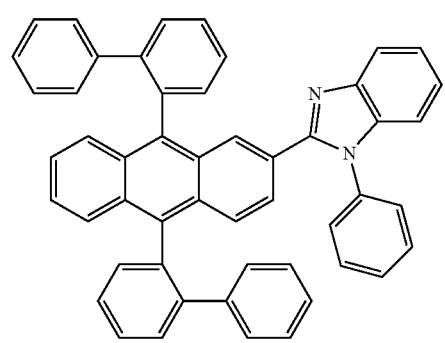
2-54
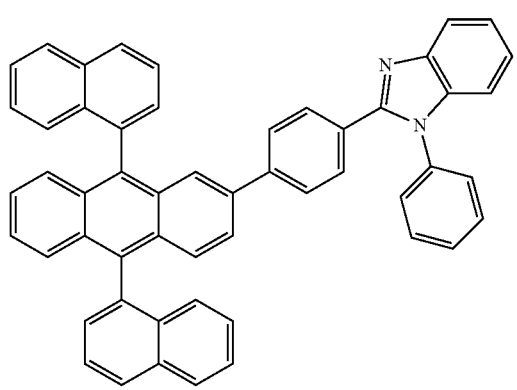

-continued
2-55
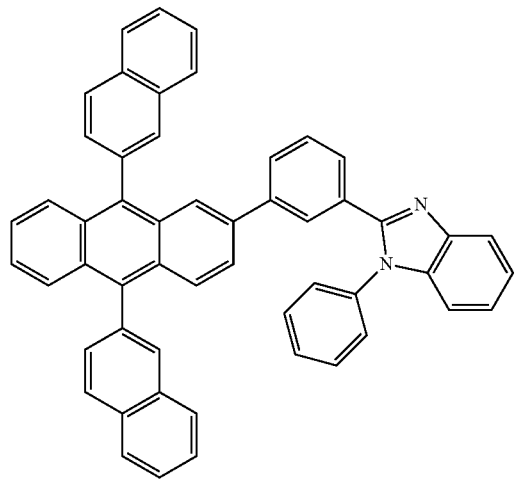
2-56
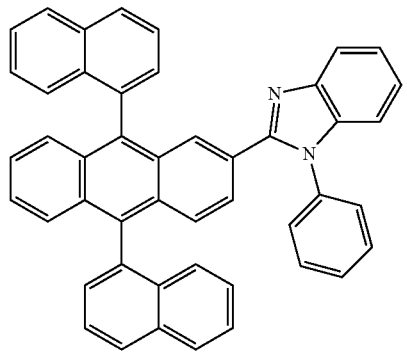
2-57
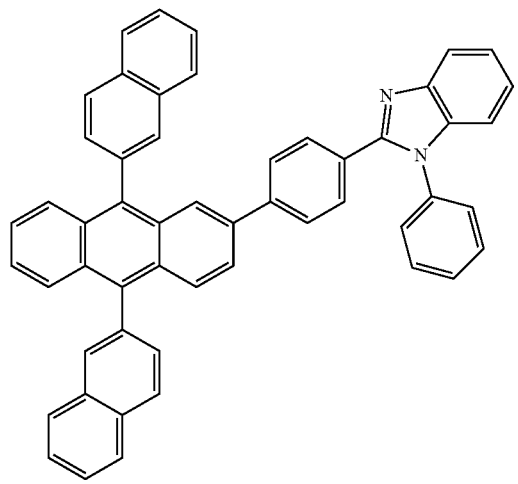
2-58
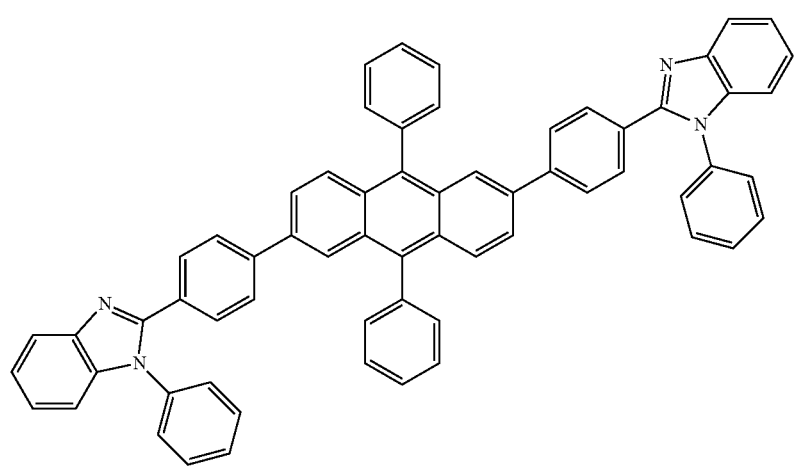

2-59
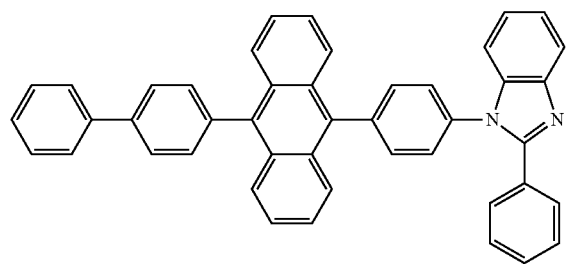
2-60
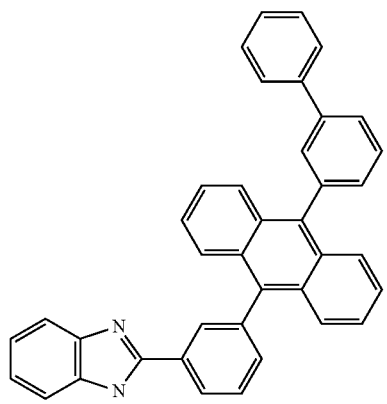
Specific examples of the phenanthroline derivative having one or more phenanthroline rings represented by Formula (3) include any of compounds represented in Formulas (3-1 to 3-14) given below.
3-1
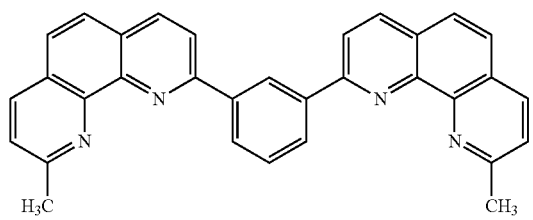
3-4
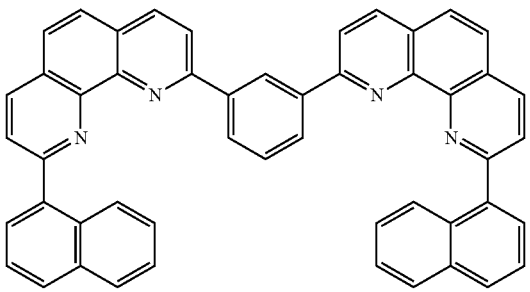
3-2
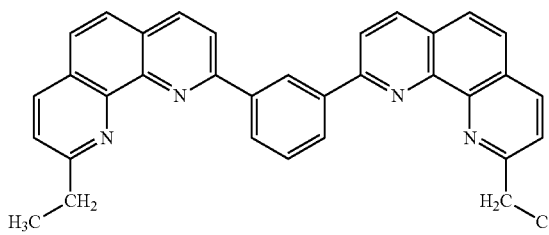
3-5
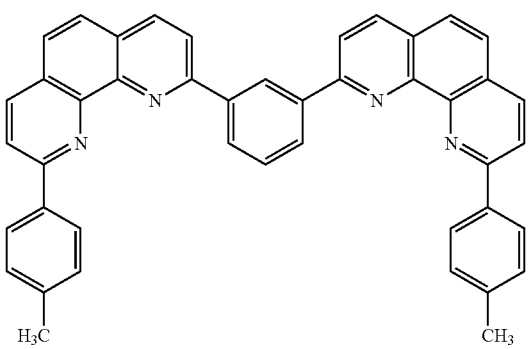
3-3
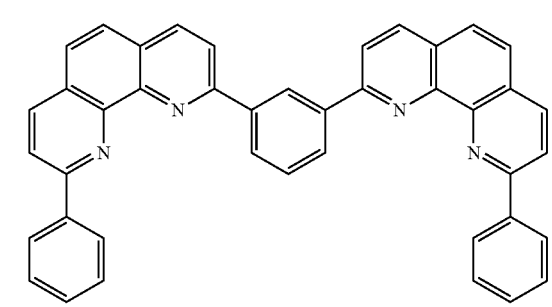
3-6
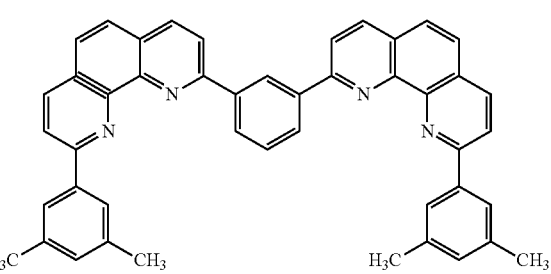

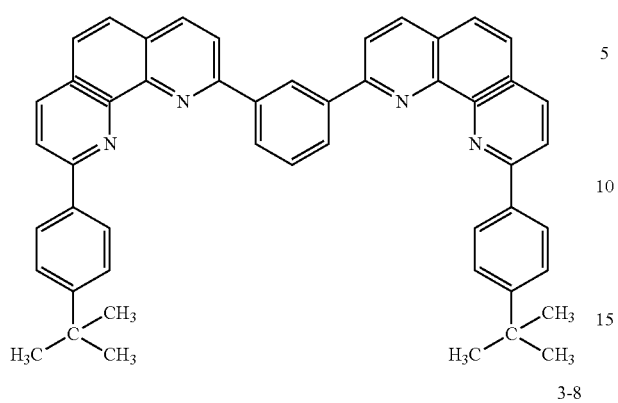

3-7

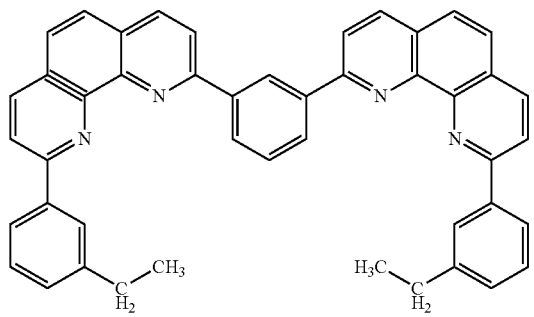

3-8

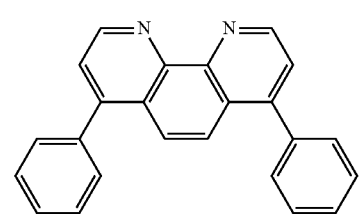

3-9

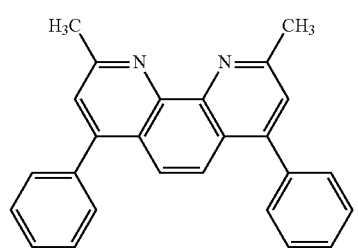

3-10

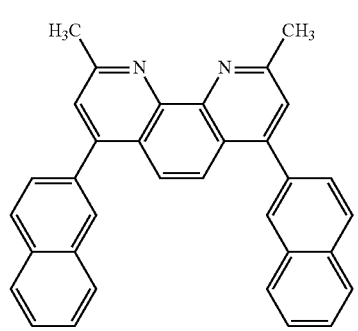

3-11

3-12

3-13

3-14

The thickness of each of the first layer 15A and the second layer 15B depends on an overall configuration of the organic EL device 10; however, the first layer 15A may be preferably greater than the second layer 15B in thickness. For example, the thickness of the first layer 15A may be preferably at least 10 nm but no more than 280 nm. The thickness of the second layer 15B may be preferably 5 nm or more, and may be more preferably at least 5 nm but no more than 10 nm.

A constituent material of the cathode 20 may be a material having a small work function and the light-transmissive property. The specific example material includes alkali metal oxide such as $LiO_2$, $Cs_2O_3$, $Cs_2SO_4$, $MgF$, $LiF$, and $CaF_2$, alkali metal fluoride, alkali earth metal oxide, and alkali earth fluoride. As an alternative, a light-transmissive reflecting material like alloy (for example, MgAg) containing aluminum (Al), calcium (Ca), or magnesium (Mg) may be used. The cathode 20 may be configured to be a single layer including any one of the above-described materials, or to include a plurality of laminated layers including any of the above-described materials. In the case of a laminated structure, by forming, for example, an IZO film or a transparent $SiN_x$ film as an upper layer, it is possible to improve the conductivity, and to suppress deterioration in the electrodes.

It is to be noted that the cathode 20 may be provided independently for each of the sub-pixels 5R, 5G, and 5B that configure each of the pixels 5. Alternatively, the cathode 20 may be formed in the shape of a continuous film inside the display region 110 to be used as a common electrode for the plurality of pixels 5. Further, in a case where the organic EL device 10 is of a cavity structure, a semi-transmissive and semi-reflective material may be preferably used for the cathode 20. As a result, the emitted light that is subjected to multiple interference between a light-reflecting surface on the side of the anode 12 and a light-reflecting surface on the side of the cathode 20 is extracted from the cathode 20 side. In this case, an optical distance between the light-reflecting surface on the side of the anode 12 and the light-reflecting surface on the side of the cathode 20 is defined by a wavelength of the light to be extracted, and a thickness of each layer should be set up to satisfy such an optical distance. In such a top-emission organic EL device, by using the cavity structure in a proactive manner, it is possible to improve the efficiency of extracting light to the outside, and to perform control of the emission spectrum, for example.

A protective layer 28 has a thickness of, for example, at least 1 μm but no more than 3 μm, and may be made of any of an insulating material or a conductive material. For the insulating material, an inorganic amorphous insulating material such as amorphous silicon (α-Si), amorphous silicon carbide (α-SiC), amorphous silicon nitride (α-$Si_{1-x}N_x$), and amorphous carbon (α-C) may be preferable. Since such an inorganic amorphous insulating material makes up no grain, it has low water permeability, and thus serves as a superior protective film. Other than the above, a silicon nitride (typically, $Si_3N_4$) film, a silicon oxide (typically, $SiO_2$) film, a silicon nitrided oxide (SiNxOy: composition ratio X>Y) film, a silicon nitric oxide (SiOxNy: composition ratio X>Y) film, a thin film containing carbon like DLC (Diamond-Like Carbon) as a major constituent, a CN (Carbon Nanotube) film, or any other equivalent film is used.

A sealing layer 29 is formed almost evenly on the protective layer 28 to serve as an adhesive layer. The sealing layer 29 is made of, for example, epoxy resin or acrylic resin.

The counter substrate 31 is located on the side of the cathode 20 of the organic EL device 10 to seal the organic EL devices 10 along with the sealing layer 29. The counter substrate 31 is made of a material such as glass that is transparent with respect to light that is generated by the organic EL devices 10. The counter substrate 31 is provided with, for example, a light-shielding film acting as a black matrix 32, and a color filter 33. The counter substrate 31 extracts the light that is generated by the organic EL devices 10, and absorbs any outside light reflected in a wiring pattern between each of the organic EL devices 10, resulting in the contrast being improved.

A light-shielding film 32 is made of, for example, a black resin film with a black coloring agent mixed therein and with the optical density of 1 or more, or a thin-film filter utilizing thin-film interference. A configuration with use of the black resin film allows the light-shielding film 32 to be formed less expensively and easily, and therefore such a configuration may be preferable. The thin-film filter includes one or more laminated thin films each of which is made of, for example, metal, metal nitride, or metal oxide material to attenuate light utilizing the thin-film interference. A specific example of the thin-film filter includes a filter with Cr and chromium oxide (III) ($Cr_2O_3$) laminated alternately thereon.

The color filter 33 has a red filter, a green filter, and a blue filter that are disposed in this order. Each of the red filter, the green filter, and the blue filter is formed in a rectangular shape without any gap, for example. Each of the red filter, the green filter, and the blue filter is made of a resin material with mixed pigment, and is adjusted in such a manner that the optical transmittance in intended red, green, or blue wavelength band is raised, and the optical transmittance in any other wavelength band is lowered by selecting the pigment. It is to be noted that, on the organic EL device 10 that is provided on each of the sub-pixels 5R, 5G, and 5B, the color filter of the corresponding color is disposed.

Here, it is possible to form the organic layer X that is provided between the anode 12 and the cathode 20 that configure the organic EL device 10 using dry process techniques such as a vacuum evaporation method, an electron beam deposition method (EB method), a molecular beam epitaxy method (MBE method), a sputtering method, and an OVPD (Organic Vapor Phase Deposition) method.

Further, in addition to the above-described methods, it is also possible to form the organic layer X utilizing wet process techniques such as coating methods including a laser transfer method, a spin-coating method, a dipping method, a doctor blade method, a discharge-coating method, and a spray-coating method, as well as printing methods including an ink-jet method, an offset printing method, a relief printing method, an intaglio printing method, a screen printing method, and a micro-gravure coating method. Alternatively, the combined use of the dry process techniques and wet process techniques may be also permitted depending on the property of each organic layer or each member.

(1-2. Overall Configuration)

FIG. 3 illustrates a planar configuration of a display unit 10 provided with the organic EL device 10 of the embodiment. The display unit 10 is used as an organic EL television apparatus, or any other similar apparatus, and the plurality of organic EL devices 10 is disposed in a matrix pattern as the display region 110 on the drive substrate 11. At the periphery of the display region 110, a signal line driving circuit 120 and a scan line driving circuit 130 are provided as drivers for image display.

A pixel driving circuit 140 is provided inside the display region 110. FIG. 4 illustrates an example of the pixel driving circuit 140. The pixel driving circuit 140 is an active-type driving circuit that is formed in a lower layer of the anode 12. In other words, the pixel driving circuit 140 includes a drive transistor Tr1 and a write transistor Tr2; a capacitor (retention capacitance) Cs between the transistors Tr1 and Tr2; and the organic EL device 10 that is coupled to the drive transistor Tr1 in series between a first power supply line (Vcc) and a second power supply line (GND). Each of the drive transistor Tr1 and the write transistor Tr2 includes a typical thin-film transistor (TFT), and a configuration thereof may be, for example but not limited to, in an inversely-staggered structure (so-called bottom-gate type), or in a staggered structure (top-gate type).

In the pixel driving circuit 140, a plurality of signal lines 120A are disposed in a column direction, and a plurality of scan lines 130A are disposed in a row direction. A crossing point of each of the signal lines 120A and each of the scan lines 130A corresponds to any one (sub-pixel) of the respective organic EL devices 10. Each of the signal lines 120A is coupled to the signal line driving circuit 120, and image signals are supplied to a source electrode of the write transistor Tr2 through the signal lines 120A from the signal line driving circuit 120. Each of the scan lines 130A is coupled to the scan line driving circuit 130, and scan signals are sequentially supplied to a gate electrode of the write transistor Tr2 through the scan lines 130A from the scan line driving circuit 130.

In the display unit 10, scan signals are supplied to each pixel through the gate electrode of the write transistor Tr2 from the scan line driving circuit 130, and image signals are held on the retention capacitance Cs through the write transistor Tr2 from the signal line driving circuit 120. In other words, the drive transistor Tr1 is controlled to be turned on/off depending on a signal held on the retention capacitance Cs, thereby injecting a drive current Id into the organic EL device 10 to recombine holes and electrons, leading to light emission. The light passes through the anode 12 and the drive substrate 11 to be taken out in the case of the bottom-surface light emission (bottom-emission), and passes through the cathode 20, the color filter 33, and the counter substrate 31 to be taken out in the case of the top-surface light emission (top-emission).

As mentioned previously, the high image quality has been typically desired for the display units. For example, to improve the light extraction efficiency, on an inclined side surface (tapered surface) of a so-called partition that defines a light emission region, light emitted from the light-emitting device at a large angle relative to a front direction of a display surface is reflected on an interfacial surface in the display surface direction by utilizing a difference in the refractive index of the tapered surface and a filling layer that is provided on the light-emitting device, thereby attempting to improve the light extraction efficiency.

However, in a case where an organic layer such as a light-emitting layer is formed using a vapor deposition method, a thickness of the organic layer to be formed on a tapered surface becomes smaller by about one third to about one fifth in comparison with a thickness of the organic layer to be formed on a bottom surface of a light emission region that is segmented by a partition. FIG. 7 illustrates a cross-sectional configuration of a typical organic EL device 100 in which an organic layer 100X including a light-emitting layer is provided between an anode 112 and a cathode 120. As illustrated in FIG. 7, a thickness of the organic layer 100X in the vicinity of a boundary between a tapered surface of a partition 127 and the partition 127 of the light emission region that is segmented by the partition 127 becomes smaller. This causes short-circuiting between the anode 112 and a charge generation layer 116, in particular, in the vicinity of a boundary (a boundary part P) between the tapered surface of the partition 127 and the partition 127 of the light emission region that is segmented by the partition 127, which degrades the current efficiency of a light-emitting layer that is formed on the organic layer 100X side, resulting in deterioration in the light emission efficiency.

It is likely that the short-circuiting in the boundary part P will occur especially in the organic EL device 10 in which a reflector structure is formed on the anode 12, as described in the present embodiment. The reflector structure makes it possible to reduce power consumption by providing the plurality of openings 27A on the anode 12, as illustrated in FIG. 2. In other words, providing the plurality of openings 27A may possibly make an aperture ratio lower as compared with a case where the single large opening 27A is formed; however, it is possible to make the luminance of the sub-pixels 5R, 5G, and 5B equivalent by raising the light extraction efficiency as described above. Specifically, for example, even if the aperture ratio falls to one-half by providing the plurality of openings 27A, it is possible to make the luminance of the sub-pixels 5R, 5G, and 5B equivalent without changing the current density in the light-emitting layer 14 with a twofold increase in the light extraction efficiency. In such a manner, it is possible to reduce power consumption by lowering the aperture ratio while keeping the current density in the light-emitting layer 14. Further, for example, in a case where the light extraction efficiency is increased more than twice even if the aperture ratio falls to one-half, it is possible to make the luminance of the sub-pixels 5R, 5G, and 5B equivalent even if the current density in the light-emitting layer 14 is lowered. In this case, further reduction in the power consumption is achieved. In addition, this makes it possible to suppress aging of light emission properties (so-called burn-in). More specifically, an organic EL layer configuring the light-emitting layer 14 is typically more likely to be subjected to aging with an increase in the current density, and thus such a layer is less likely to be subjected to aging by lowering the current density, which allows the image quality to be improved.

In such a manner, low power consumption and enhanced image quality is achieved by forming the reflector structure on the anode 12; however, it is likely that the short-circuiting will occur in the vicinity of a circumferential area of a bottom of the opening 27A, resulting in the current efficiency being possibly deteriorated as described above. This is because a length of a borderline between the anode 12 and the partition 27 is increased by providing the plurality of openings 27A as compared with a case where a single large opening is formed. Specifically, for example, if the rectangular opening 27A is formed on the anode 12 of 2 millimeters square, the borderline between the anode 12 and the opening 27A becomes about 8 millimeters in length. On the contrary, for example, if four openings 27A each with a diameter of one millimeter are formed, for example, as illustrated in FIG. 5B, the length of the borderline becomes 12.6 millimeters equivalent to an about 1.5 times increase. For example, if nine openings 27A each with a diameter of 0.66 millimeter are formed, for example, as illustrated in FIG. 5C, the length of the borderline becomes 18.6 millimeters equivalent to an about 2.3 times increase.

To efficiently extract light by reflection on the tapered surface of the partition 27, it may be preferable that the opening 27A be in the curved surface shape as viewed from a top surface thereof, and be in the circular shape as illustrated in FIGS. 5A to 5C, for example. Further, it is possible to extract light efficiently by making a diameter of each of the openings 27A similar to a thickness of the partition 27 that forms the tapered surface. As a result, the diameter of the opening 27A is within the range of several micrometers to several tens of micrometers, and, for example, if the openings 27A are formed in a densely-packed manner on the anode 12 of 2 millimeters square, several tens of thousands to hundreds of thousands of openings 27A are formed. Therefore, it is asked to suppress occurrence of short-circuiting in the vicinity of a circumferential area of a bottom of the opening 27A, in particular, in the vicinity of a boundary between the anode 12 and the opening 27A.

On the contrary, in the present embodiment, a structure is provided in which a layer having the orientation, a layer having the high nitrogen-containing rate and the low orientation, and a layer including a metal element are laminated in this order from the light-emitting layer 14 side on the light-emitting layer 14 on the opposite side of the anode 10. Specifically, the first layer 15A that contains a polycyclic aromatic hydrocarbon compound having the orientation, and the second layer 15B that contains a larger amount of nitrogen element than the first layer are provided as the electron supply layer 15 between the light-emitting layer 14 and the cathode 20 representing the layer including a metal element. In particular, the efficiency of injecting electrons from the cathode 20 into the electron supply layer 15 is improved by making up the second layer 15B on the side of the cathode 20 with a material containing a larger amount of nitrogen element. Further, by providing the first layer 15A including the polycyclic aromatic hydrocarbon compound having the orientation on the side of the light-emitting layer 14, migration of electrons from the cathode 20 to the light-emitting layer 14, more specifically, migration of the electrons injected from the cathode 20 into the second layer 15B from the second layer 15B to the light-emitting layer 14 is carried out more easily. This is achieved because steric hindrance of the polycyclic aromatic hydrocarbon compound to be used as a constituent material of the first layer 15A is small. The polycyclic aromatic hydrocarbon compound is reduced in steric hindrance thereof, and thus molecular turn is less likely to be limited. Therefore, π-conjugated electrons come close to one another with ease, leading to the improved orientation. As a result, electrons are easy to flow relative to an electric field to be applied in one direction (from the anode 10 to the blue light-emitting layer 14), which makes it possible to suppress flow of the electrons in a traverse direction, that is, occurrence of short-circuiting in the vicinity of a boundary between the cathode 20 and the opening 27A.

As described above, in the organic EL device 10 and the display unit 1 of the present embodiment, the electron supply layer 15 is configured in a laminated structure in which the first layer 15A that contains the polycyclic aromatic hydrocarbon compound having the orientation, and the second layer 15B that contains a larger amount of nitrogen element than the first layer are stacked. This improves flow of charges (electrons) between the electrode and the light-emitting layer, specifically in the present embodiment, between the cathode 20 and the light-emitting layer 14. As a result, migration of the electrons toward a planar surface direction of an organic layer A is suppressed, and occurrence of short-circuiting in a thin-film region of the organic layer A, specifically, in the vicinity of the boundary between the anode 12 and the opening 27A is suppressed. This makes it possible to improve the current efficiency of the display unit 1.

It is to be noted that the invention is not limited to the structure of the organic EL device 10 represented in the above-described embodiment, and is also applicable to an organic EL device of a so-called tandem structure in which two light-emitting layers are laminated.

Hereinafter, the description is provided on modification examples 1 and 2 of the disclosure. Any component parts same as those in the above-described embodiment are denoted with the same reference numerals, and the related descriptions are omitted as appropriate.

[2. Modification Examples]
(2-1. Modification Example 1)

FIG. 8 illustrates a cross-sectional configuration of an organic EL device 10A according to a modification example 1 of the disclosure. The organic EL device 10A has a configuration in which an anode 12, an organic layer X, and a cathode 20 are laminated in this order on a drive substrate 11, as with the above-described embodiment. However, the present modification example is different from the above-described embodiment in that a metal doped layer 19 is provided between the organic layer X and the cathode 20, specifically, between the second layer 15B and the cathode 20.

The metal doped layer 19 serves to form, for example, an interface state or an electric double layer between the cathode 20 and the second layer 15B, or to raise the efficiency of injecting electrons into the second layer 15B with the help of a tunnel effect, and to improve the mobility of the electrons injected from the cathode 20 to the metal doped layer 19. Further, the metal doped layer 19 also has a function acting as an n-layer of a charge generation layer. Examples of a material for the metal doped layer 19 include lithium oxide ($LiO_2$) that is oxide of lithium (Li), cesium carbonate ($Cs_2CO_3$) that is composite oxide of cesium (Cs), and a mixture of those oxide and composite oxide materials. Further, a constituent material of the metal doped layer 19 is not limited to such materials. For example, alkali earth metal such as calcium (Ca) and barium (Ba), alkali metal such as lithium and cesium, metal having a small work function such as indium (In) and magnesium (Mg), or oxide, composite oxide, and fluoride of any of those metal materials may be used as a simple substance, or a mixture or alloy of any of such metal, oxide, composite oxide, and fluoride materials may be used to enhance the stability. Further, for example, a material in which Li, Al, or Mg is doped to a phenanthroline derivative (for example, Formula 3-3) may be used. A thickness of the metal doped layer 19 depends on an overall configuration of the organic EL device 10A; however, may be preferably, for example, at least 5 nm but no more than 50 nm.

As described above, in the present modification example, the metal doped layer 19 is provided between the second layer 15B and the cathode 20. As a result, the organic EL device 10A of the present modification example makes it possible to reduce a drive voltage, thereby allowing for a prolonged operating life thereof, in addition to the effects of the above-described embodiment. Further, the metal doped layer 19 provides an effect of improving the adhesiveness on an interfacial surface with the cathode 20 having a convex-concave structure with an increase in the chemical interaction due to properties of a constituent material.

(2-2. Modification Example 2)

FIG. 9 illustrates a cross-sectional configuration of an organic EL device 10B according to a modification example 2 of the disclosure. The organic EL device 10B has a configuration in which an anode 12, an organic layer X, and a cathode 20 are laminated in this order on a drive substrate 11, as with the above-described embodiment. However, the present modification example is different from the above-described embodiment and the modification example 1 in that the organic layer X is of a tandem structure in which an organic layer A and an organic layer B are laminated with a charge generation layer 16 (connecting layer) in between.

Typically, in the organic EL device 10B having the tandem structure, a thickness of the organic layer X (organic layer A and organic layer B) becomes greater as compared with the organic EL device 10 in which a light-emitting layer (light-emitting layer 14) is provided one by one as described above. Therefore, it is unlikely that short-circuiting between the anode 12 and the cathode 20 will occur in the vicinity of a circumferential area of a bottom of a light emission region that is segmented by a partition 27.

In the organic EL device 10B, the organic layer A and the organic layer B are laminated with the charge generation layer 16 in between, as described above. The organic EL device 10B has a configuration in which the anode 12, the organic layer A, the charge generation layer 16, the organic layer B, and the cathode 20 are laminated in this order on the drive substrate 11. Among these, in the organic layer A and the organic layer B, for example, hole supply layers 13 and 17, light-emitting layers (blue light-emitting layer 14B and yellow light-emitting layer 14Y), and electron supply layers 15 and 18 are laminated, respectively, in this order from the anode 12 side. Here, the description is provided on each of those layers on the assumption that the light-emitting layers included in the organic layer A and the organic layer B are the blue light-emitting layer 14B and the yellow light-emitting layer 14Y, respectively.

Each of the hole supply layer 13 and the electron supply layer 15 that configure the organic layer A has a configuration similar to a configuration in the above-described embodiment, and a material to be used for the blue light-emitting layer mentioned for the above-described light-emitting layer 14 is applicable to the blue light-emitting layer 14B. Further, also for the hole supply layer 17 that configures the organic layer B, a configuration and a material similar to those of the hole supply layer 13 are applicable.

The charge generation layer 16 serves to couple the organic layer A and the organic layer B with each other. A constituent material of the charge generation layer 16 is selected as appropriate depending on the properties of the adjacent organic layer A (specifically, the electron supply layer 15) and the adjacent organic layer B (specifically, the hole supply layer 17), and the charge generation layer 16 is formed as a laminated structure including, for example, a layer using a material having the electronic donor property and a layer using a material having the electronic acceptor property. As the material having the electronic donor property, for example, it is possible to use a material having the electron transport property doped with N-type dopant, specifically, any of materials cited for the above-described electron transport layers 14d1 and 14d2, for example. Examples of the N-type dopant material include alkali metal, alkali earth metal, or oxide, composite oxide, fluoride, and organic complexes of any of those metal materials. As the material having the electronic acceptor property, for example, a material having the hole transport property doped with P-type dopant is used. For the material having the hole transport property, for example, it is possible to use any of the materials cited for the hole supply layers 13 and 17. Examples of the P-type dopant material include 7,7,8,8-tetracyano-2,3,5,6-tetrafluoroquinodimethane (F4-TCNQ) and hexaazacyanotriphenylene (HAT-6CN). A thickness of the charge generation layer 16 depends on an overall configuration of the organic EL device 10B; however, may be preferably, for example, at least 1 nm but no more than 100 nm, and may be more preferably at least 10 nm but no more than 50 nm.

The yellow light-emitting layer 18 is made of at least one kind of light emission material having one or more peak wavelengths at any of a region of, for example, at least 500 nm but no more than 750 nm. A thickness of the yellow light-emitting layer 18 depends on an overall configuration of the organic EL device 10; however, may be preferably, for example, at least 10 nm but no more than 200 nm, and may be more preferably at least 15 nm but no more than 100 nm.

For the electron supply layer 18, a configuration similar to that of the electron supply layer 15 that configures the organic layer A may be used. However, for example, the electron supply layer 18 has a configuration in which, for example, a layer including a material having the electron transport property (electron transport layer, not illustrated) and a layer including a material having the electron injection property (electron injection layer, not illustrated) are laminated. A thickness of the electron supply layer 19 depends on an overall configuration of the organic EL device 10B; however, may be preferably, for example, at least 10 nm but no more than 50 nm. In the case of a laminated structure of the electron transport layer and the electron injection layer, a thickness of the electron transport layer may be preferably, for example, at least 10 nm but no more than 200 nm, and may be more preferably at least 20 nm but no more than 180 nm. Further, a thickness of the electron injection layer may be preferably, for example, 5 nm or more. This makes it possible to perform sufficient electron injection even in a pixel having the considerable irregularity.

For a constituent material of the electron transport layer, it may be preferable to use an organic material having the superior electron transport capability and the high contact property with the cathode 20. For example, it may be preferable to use imidazole derivative, and phenanthroline derivative having one or more phenanthroline rings as represented by Formulas (2) and (3) given above. This stabilizes supply of the electrons to the light-emitting layer 18.

For a constituent material of the electron injection layer, it is possible to use alkali earth metal such as calcium (Ca) and barium (Ba), and alkali metal such as lithium, sodium, and cesium. Alternatively, oxide, complex oxide, and fluoride of any of those metal materials may be used as a simple substance, or a mixture or alloy of any of such metal, oxide, complex oxide, and fluoride materials may be used to enhance the stability.

As described above, in the organic EL device having a tandem structure, a thickness of an organic layer between the anode 12 and the cathode 20 becomes greater, and thus it is unlikely that short-circuiting between the anode 12 and the cathode 20 will occur. However, the charge generation layer 16 that is provided between the organic layer A and the organic layer B is made of a material having the high conductivity as described above, which may possibly cause the short-circuiting between the anode 12 and the charge generation layer 16.

Therefore, a thickness between the charge generation layer 16 and the blue light-emitting layer 14B may be preferably formed to become greater than a thickness between the yellow light-emitting layer 14Y and the charge generation layer 16. Further, an amine-based material is used for the hole supply layer 13 in many cases, which may easily cause random orientation. Therefore, it may be preferable to increase a thickness of the electron supply layer 15. In other words, a thickness between the charge generation layer 16 and the blue light-emitting layer 14B may be preferably formed to become greater than a thickness between the anode 12 and the blue light-emitting layer 14. This reduces occurrence of the short-circuiting between the anode 12 and the charge generation layer 16.

The organic EL device 10B of the present modification example has a tandem structure in which the organic layer A and the organic layer B are laminated with the charge generation layer 16 in between, and the electron supply layer 15 that configures the organic layer A on the lower-layer side (anode 12 side) is configured in a similar manner to the electron supply layer 15 in the above-described embodiment, thereby suppressing occurrence of the short-circuiting in the vicinity of a boundary between the anode 12 and the opening 27A. This makes it possible to improve the current efficiency of the display unit provided with the organic EL device 10B.

Further, in a case where the light-emitting layer to be provided in the organic layer A is the blue light-emitting layer 14B, flow of electrons between the cathode 20 and the blue light-emitting layer 14B is improved, which raises the light emission efficiency of the blue light-emitting layer. In addition, in the present modification example, a tandem structure in which two organic layers X (organic layer A and organic layer B) are laminated is adopted, leading to the improved light emission efficiency.

It is to be noted that a case where the two organic layers X are laminated is represented here; however, this is not limitative, and three or more layers may be laminated alternatively. With an increase in the number of layers to be stacked, it is possible to further improve the light emission efficiency. The theoretical light emission efficiency lm/W in the case of lamination of the two organic layers X like the present modification example is unchanged, and the current efficiency cd/A shows a twofold increase, and shows a threefold increase in the case of lamination of three layers.

[3. Working Examples]
(Working Example 1)

Next, the description is provided on working examples of the disclosure. As a working example, the organic EL devices 10B each having the tandem structure (samples 1 and 3 to 8) that are described in the modification examples, and an organic EL device having a typical configuration (sample 2) to be used as a comparative example were fabricated. Thereafter, measurement was made, for each of the devices, for the voltage in the current density of 10 mA cm$^{-2}$ and the light emission efficiency (cd/A, Table 1) in the current density of 0.1 mA cm$^{-2}$, the light emission efficiency (cd/A, Table 2) in the current density of 0.1 mA cm$^{-2}$ for the blue light-emitting layer 14B, and a relationship between each wavelength and the light emission intensity (FIG. 9).

The hole supply layer 13 and the blue light-emitting layer 14B were formed as the organic layer A on the anode 12 in which the plurality of openings 27A were formed, and thereafter a hole block layer that is made of an amine-based material was formed, for example. Afterward, an anthracene derivative (for example, Formula 1-85) was formed at deposition rate of 0.1 to 30 nm/sec and with a thickness of 100 nm using a vacuum evaporation method, and thereafter a phenanthroline derivative (for example, Formula 3-3) was formed at deposition rate of 0.1 to 1 nm/sec and with a thickness of 10 nm using the vacuum evaporation method. Next, a film including the phenanthroline derivative and lithium (Li) was formed as the charge generation layer 16 with a thickness of 10 nm using co-evaporation at a ratio of 96 to 4, and a film including an azatriphenylene derivative (for example, Formula 4) was formed at deposition rate of 0.01 to 1 nm/sec and with a thickness of 5 nm using the vacuum evaporation method. Subsequently, the hole supply layer 17, the yellow light-emitting layer 14Y, as well as a film including the phenanthroline derivative (for example, Formula 3-3) and lithium (Li) formed using co-evaporation at a ratio of 96 to 4 were formed as the organic layer B with a thickness of 20 nm, and thereafter a Ca film was formed with a thickness of 2.5 nm, and further an IZO film was formed as the cathode 20 using a sputtering method. Afterward, an SiNx film was formed as the insulating layer 28 using a CVD method, and thereafter the sealing layer 29 was formed using a material having the high refractive index to obtain the organic EL devices 10B (sample 1). The samples 3 to 8 were also fabricated in the similar manner as the above-described method.

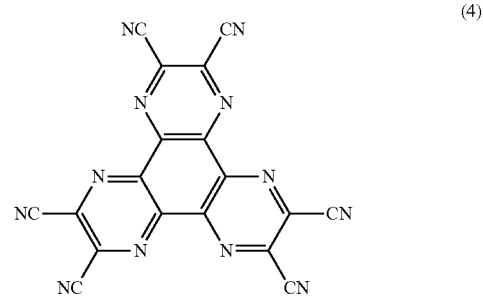 [SMILES: N#Cc1nc2c3nc(C#N)c(C#N)nc3c3nc(C#N)c(C#N)nc3c2nc1C#N]

(4)

As the comparative example (sample 2), first, the hole supply layer 13 and the blue light-emitting layer 14B were formed as the organic layer A on the anode 12 in which the plurality of openings 27A were formed, and thereafter the hole block layer that is made of, for example, an amine-based material was formed. Next, a film including a phenanthroline derivative (for example, Formula 3-3) was formed as the charge generation layer 16 at deposition rate of 0.1 to 1 nm/sec and with a thickness of 10 nm using the vacuum evaporation method, and thereafter a film including the phenanthroline derivative and lithium (Li) was formed with a thickness of 10 nm using co-evaporation at a ratio of 96 to 4, and a film including an azatriphenylene derivative (for example, Formula 4) was further formed at deposition rate of 0.01 to 1 nm/sec and with a thickness of 5 nm using the vacuum evaporation method. Subsequently, the hole supply layer 17, the yellow light-emitting layer 14Y, as well as a film including the phenanthroline derivative (for example, Formula 3-3) and lithium (Li) formed using co-evaporation at a ratio of 96 to 4 were formed as the organic layer B with a thickness of 20 nm, and thereafter a Ca film was formed with a thickness of 2.5 nm, and further an IZO film was formed as the cathode 20 using a sputtering method. Afterward, an SiNx film was formed as the insulating layer 28 using a CVD method, and thereafter the sealing layer 29 was formed using a material having the high refractive index to obtain the organic EL devices 10B (sample 2).

TABLE 1

| | Electron supply layer | | | Light emission |
| | First layer (nm) | Second layer (nm) | Voltage (V) | efficiency (cd/A) |
| --- | --- | --- | --- | --- |
| Sample 1 | 100 | 10 | 7.7 | 87 |
| Sample 2 | — | 110 | 8.0 | 33 |

TABLE 2

| | Electron supply layer | | | Blue light |
| | First layer (nm) | Second layer (nm) | Voltage (V) | emission efficiency ratio |
| --- | --- | --- | --- | --- |
| Sample 3 | 100 | 0 | 13.3 | 81 |
| Sample 4 | 100 | 1 | 13.3 | 81 |
| Sample 5 | 100 | 5 | 9.1 | 100 |
| Sample 6 | 100 | 10 | 9.1 | 100 |
| Sample 7 | 100 | 20 | 9.3 | 95 |
| Sample 8 | 100 | 30 | 9.4 | 90 |

It was seen from Table 1 that a drive voltage was reduced as compared with the sample 2 in which a single layer including the phenanthroline derivative was configured as the electron supply layer, and the light emission efficiency was improved significantly in the case where the electron supply layer 15 of the sample 1 was configured in a laminated structure in which the first layer 15A that contains, for example, the anthracene derivative as a polycyclic aromatic hydrocarbon compound, and the second layer 15B that contains a larger amount of nitrogen element than the first layer 15A, that is, contains, for example, the phenanthroline derivative are laminated.

Further, it was seen from Table 2 that the light emission efficiency of the blue light-emitting layer 14B was improved by setting the thickness of the second layer 15B at 5 nm or more. In particular, by setting the thickness within the range of at least 5 nm but no more than 10 nm, it was possible to further improve the light emission efficiency of the blue light-emitting layer 14B while suppressing a drive voltage. It is to be noted that a thickness as is defined here refers to a thickness of a layer to be formed at the bottom of the opening 27A. For example, by setting the thickness of the second layer 15B at 5 nm, the thickness of the second layer 15B to be formed on an inclined surface of the partition 27 becomes less than 5 nm, which makes it possible to suppress migration to a transverse direction of charges (electrons) injected from the charge generation layer 16 more than migration to a thickness direction thereof.

FIG. 10 illustrates the light emission intensity in each wavelength of a sample A in a case where, for example, the electron supply layer 15 was configured in a laminated structure in which the first layer 15A and the second layer 15B are laminated like the sample 5, and a thickness of each layer is set at a preferable value as described above; and a sample B in a case where the electron supply layer is configured as a single layer like the sample 2. As seen from FIG. 10, by configuring the electron supply layer 15 as two layers, the light emission intensity of blue light (within the range of about 450 nm to about 495 nm) is raised.

Further, a thickness of the first layer 15A may be preferably 50 nm or more. The polycyclic aromatic hydrocarbon compound that is a constituent material of the first layer 15A is oriented, and therefore is superior in the electron transfer property toward one direction. Consequently, even if the thickness is increased, it is unlikely that a voltage will be raised to high level. Therefore, by setting the thickness at 50 nm or more, it is possible to further reduce occurrence of the short-circuiting between the anode 12 and the charge generation layer 16.

[4. Application Examples]
(Module and Application Example)

Hereinafter, the description is provided on application examples of any of the display units provided with the organic EL devices 10, 10A, and 10B mentioned in the above-described embodiment and the modification examples thereof. Any of the display units mentioned in the above-described embodiment is applicable to display units of electronic apparatuses in various fields that display externally-inputted image signals or internally-generated image signals, as a still image or a moving image. Examples of the electronic apparatuses include television apparatuses, digital cameras, laptop personal computers, mobile terminals such as mobile phones, and video cameras.

(Module)

Any of the display units of the above-described embodiment is incorporated into various electronic apparatuses according to application examples 1 to 3 to be hereinafter described as a module as illustrated in FIG. 11, for example. This module is configured, for example, in such a manner that a region 210 exposed from a protective layer 30 and a sealing substrate 40 is provided on one side of a substrate 11, and external connection terminals (not illustrated) is formed at this exposed region 210 by extending wiring patterns of a signal line driving circuit 120 and a scan line driving circuit 130. An FPC (Flexible Printed Circuit) board 220 for signal input/output may be provided at these external connection terminals.

(Application Example 1)

FIGS. 12A and 12B each illustrate an appearance of a smartphone 220 according to the application example 1. For example, the smartphone 220 has a display section 221 and an operating section 222 on the front side, and a camera 223 on the backside, and any of the display units 10, 10A, and 10B of the above-described embodiment, etc. is mounted on the display section 221.

(Application Example 2)

FIGS. 13A and 13B each illustrate an appearance configuration of a tablet. The tablet includes, for example, a display section 310 (display unit 1) and a non-display section (housing) 320, as well as an operating section 130. The operating section 330 may be provided on the front side of the non-display section 320 as illustrated in FIG. 13A, or may be provided on the top surface of the non-display section 320 as illustrated in FIG. 13B. Any of the display units 10, 10A, and 10B may be mounted on a PDA or any other similar apparatus having a configuration similar to that of the tablet illustrated in FIGS. 13A and 13B.

(Application Example 3)

FIG. 14 illustrates an appearance configuration of a laptop personal computer. The personal computer includes, for example, a main unit 410, a keyboard 420 for operation of entering characters or any other information, and a display section 430 (display unit 1) for displaying images.

The disclosure is described thus far with reference to the embodiment, the modification examples, and the working examples; however, the disclosure is not limited to the above-described embodiment and the like, but various modifications may be made.

For example, a material and thickness of each layer, or film-forming methods as well as film-forming conditions, and others that are described in the above-described embodiment and the like are not limitative, and any other materials and thicknesses, or any other film-forming methods and film-forming conditions may be applicable.

Further, in the above-described embodiment and the like, the description is provided by referring to a specific example of a configuration of the organic EL device 10; however, it is not necessary to provide all the layers, and any other layer may be further provided.

Moreover, in the above-described embodiment and the like, the description is provided on the case of the active-matrix display unit; however, the disclosure is also applicable to a passive-matrix display unit. Further, a configuration of the pixel driving circuit for the active-matrix drive is not limited to the configuration mentioned in the above-described embodiments, and capacitors or transistors may be added where appropriate. In such a case, depending on modification of the pixel driving circuit, necessary driving circuit may be added in addition to the above-described signal line driving circuit 120 and scan line driving circuit 130.

It is to be noted that the effects described herein are merely exemplified and non-limiting, and other effects may be provided.

It is to be noted that the technology may be configured as follows.

[1]

An organic EL device including:

a first electrode and a second electrode; and an organic layer provided between the first electrode and the second electrode, the organic layer including a light-emitting layer, in which the organic layer includes, between the first electrode and the light-emitting layer, a first layer that contains a polycyclic aromatic hydrocarbon compound having orientation, and a second layer that contains a larger amount of nitrogen element than the first layer.

[2]

The organic EL device according to [1], in which the first layer and the second layer are laminated in this order from light-emitting layer side.

[3]

The organic EL device according to [1] or [2], in which a thickness of the first layer is greater than a thickness of the second layer.

[4]

The organic EL device according to any one of [1] to [3], including a metal doped layer between the first layer and the second layer.

[5]

The organic EL device according to any one of [1] to [4], in which the first layer includes one or more kinds of anthracene derivatives represented by Formula (1).

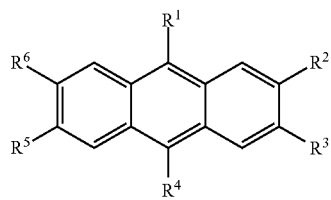
(1)

(Each of R1 to R6 is: one of a hydrogen atom, a halogen atom, a hydroxyl group, a cyano group, and a nitro group; one of a group with carbon number of 50 or less having a carbonyl group, a group with carbon number of 50 or less having a carbonyl ester group, an alkyl group with carbon number of 50 or less, an alkenyl group with carbon number of 50 or less, an alkoxyl group with carbon number of 50 or less, and derivatives thereof; or one of a group with carbon number of 30 or less having a silyl group, a group with carbon number of 30 or less having an aryl group, a group with carbon number of 30 or less having a heterocyclic group, a group with carbon number of 30 or less having an amino group, and derivatives thereof. It is to be noted that, in a case where any of the above-described substituent groups is to be used, the carbon number includes the carbon number of the substituent group to be used.)

[6]

The organic EL device according to any one of [1] to [5], in which the second layer includes one or more kinds of at least one of imidazole derivatives represented by Formula (2) and phenanthroline derivatives having one or more phenanthroline rings represented by Formula (3).

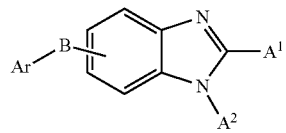
(2)

(A1 and A2 are independent from each other, and each of them is: one of a hydrogen atom and a halogen atom; or one of an alkyl group with carbon number of 1 to 20, an aromatic hydrocarbon group with carbon number of 6 to 60, a nitrogen-containing heterocyclic group with carbon number of 6 to 60, an alkoxyl group with carbon number of 1 to 20, and derivatives thereof. n is an integer in a range of 0 to 4, and m is an integer in a range of 0 to 2. B is one of an arylene group with carbon number of 60 or less, a pyridynylene group with carbon number of 60 or less, a quinolynylene group with carbon number of 60 or less, a fluorenylene group with carbon number of 60 or less, and derivatives thereof. Ar is one of an alkyl group with carbon number of 1 to 20, an alkoxyl group with carbon number of 1 to 20, an aromatic hydrocarbon group with carbon number of 6 to 60, a heterocyclic group with carbon number of 3 to 60, and derivatives thereof.)

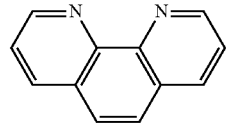
(3)

[7]

The organic EL device according to any one of [1] to [6], in which orientation of a compound configuring the second layer is lower than orientation of a compound configuring the first layer.

[8]

The organic EL device according to any one of [1] to [7], in which, in the organic layer, a thickness between the first electrode and the light-emitting layer is greater than a thickness between the second electrode and the light-emitting layer.

[9]

The organic EL device according to any one of [1] to [8], including a plurality of light emission regions on the second electrode.

[10]

The organic EL device according to [9], in which the light emission region is provided by an opening of an insulating layer that is provided on the second electrode.

[11]

The organic EL device according to [11], in which the insulating layer has an inclined surface that provides the opening, and the inclined surface relative to an electrode surface of the second electrode has an angle of 45 degrees or more.

[12]

The organic EL device according to [10] or [11], in which the opening has a circular shape.

[13]

The organic EL device according to any one of [1] to [12], in which the organic layer has a plurality of light-emitting layers, and a connecting layer is inserted among the plurality of light-emitting layers.

[14]

The organic EL device according to [13], in which the organic layer has, in order from first electrode side, a first light-emitting layer and a second light-emitting layer with the connecting layer in between, and a thickness between the first electrode and the first light-emitting layer is greater than a thickness between the connecting layer and the first light-emitting layer.

[15]

The organic EL device according to [14], in which a thickness between the second light-emitting layer and the connecting layer is greater than a thickness between the first light-emitting layer and the connecting layer.

[16]

The organic EL device according to [14] or [15], in which the first light-emitting layer is a yellow light-emitting layer, and the second light-emitting layer is a blue light-emitting layer.

[17]

An organic EL display unit with a plurality of organic EL devices,
the organic EL devices each including:
a first electrode and a second electrode; and
an organic layer provided between the first electrode and the second electrode, the organic layer including a light-emitting layer, in which
the organic layer includes, between the first electrode and the light-emitting layer,
a first layer that contains a polycyclic aromatic hydrocarbon compound having orientation, and
a second layer that contains a larger amount of nitrogen element than the first layer.

This application claims the priority on the basis of Japanese Patent Application No. 2014-245945 filed on Dec. 4, 2014 in Japan Patent Office, the entire contents of which are incorporated in this application by reference.

Those skilled in the art could assume various modifications, combinations, subcombinations, and changes in accordance with design requirements and other contributing factors. However, it is understood that they are included within a scope of the attached claims or the equivalents thereof.

The invention claimed is:

1. An organic electroluminescence (EL) device, comprising:
a first electrode;
a second electrode;
an organic layer between the first electrode and the second electrode, wherein the organic layer includes:
a hole supply layer on the second electrode;
a plurality of light-emitting layers;
an electron supply layer on a first light-emitting layer of the plurality of light-emitting layers, wherein the electron supply layer includes a first layer and a second layer; and
a connecting layer between the first light-emitting layer and a second light-emitting layer of the plurality of light-emitting layers, wherein
the connecting layer includes a laminated structure, and
the laminated structure includes an electronic donor layer that has an electronic donor property, and an electronic acceptor layer that has an electronic acceptor property;
a plurality of light emission regions on the second electrode; and
an insulating layer on the second electrode, wherein
each light emission region of the plurality of light emission regions corresponds to an opening in the insulating layer,
a length of a diameter of the opening of the insulating layer is similar to a thickness of the insulating layer,
a thickness of the first layer is greater than a thickness of the hole supply layer,
the first layer contains a polycyclic aromatic hydrocarbon compound having a first orientation, and
the second layer contains a larger amount of nitrogen element than the first layer.

2. The organic EL device according to claim 1, wherein the first layer and the second layer are laminated in order from a side of the first light-emitting layer.

3. The organic EL device according to claim 1, wherein the thickness of the first layer is greater than a thickness of the second layer.

4. The organic EL device according to claim 1, wherein the first layer includes one or more kinds of anthracene derivatives represented by Formula (1)

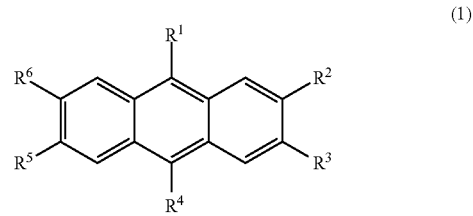

(1)

where each of R1 to R6 is:
one of a hydrogen atom, a halogen atom, a hydroxyl group, a cyano group, or a nitro group;
one of a group with carbon number of 50 or less having a carbonyl group, a group with carbon number of 50 or less having a carbonyl ester group, an alkyl group with carbon number of 50 or less, an alkenyl group with carbon number of 50 or less, an alkoxyl group with carbon number of 50 or less, or derivatives thereof; or
one of a group with carbon number of 30 or less having a silyl group, a group with carbon number of 30 or less having an aryl group, a group with carbon number of 30 or less having a heterocyclic group, a group with carbon number of 30 or less having an amino group, or derivatives thereof.

5. The organic EL device according to claim 1, wherein the second layer includes one or more kinds of at least one of imidazole derivatives represented by Formula (2) and phenanthroline derivatives having one or more phenanthroline rings represented by Formula (3),

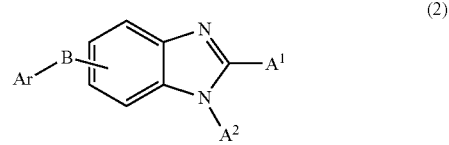

(2)

A1 and A2 are independent from each other, and
each of the A1 and the A2 is:
one of a hydrogen atom and a halogen atom; or
one of an alkyl group with carbon number of 1 to 20, an aromatic hydrocarbon group with carbon number of 6 to 60, a nitrogen-containing heterocyclic group with carbon number of 6 to 60, an alkoxyl group with carbon number of 1 to 20, or derivatives thereof, n is an integer in a range of 0 to 4 and m is an integer in a range of 0 to 2, B is one of an arylene group with carbon number of 60 or less, a pyridynylene group with carbon number of 60 or less, a quinolynylene group with carbon number of 60 or less, a fluorenylene group with carbon number of 60 or less, or derivatives thereof, and Ar is one of an alkyl group with carbon number of 1 to 20, an alkoxyl group with carbon number of 1 to 20, an aromatic hydrocarbon group with carbon number of 6 to 60, a heterocyclic group with carbon number of 3 to 60, or derivatives thereof

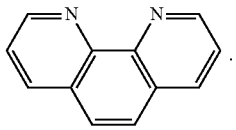

(3)

6. The organic EL device according to claim 1, wherein the second layer includes a compound having a second orientation, and the second orientation is lower than the first orientation.

7. The organic EL device according to claim 1, wherein, in the organic layer, a thickness between the first electrode and the first light-emitting layer is greater than a thickness between the second electrode and the first light-emitting layer.

8. The organic EL device according to claim 1, wherein the insulating layer has an inclined surface that has the opening, and the inclined surface has an angle of at least 45 degrees relative to an electrode surface of the second electrode.

9. The organic EL device according to claim 1, wherein the opening of the insulating layer has a circular shape.

10. The organic EL device according to claim 1, wherein a thickness between the first electrode and the second light-emitting layer is greater than a thickness between the connecting layer and the second light-emitting layer.

11. The organic EL device according to claim 10, wherein the first light-emitting layer is a blue light-emitting layer, and the second light-emitting layer is a yellow light-emitting layer.

12. An organic electroluminescence (EL) display unit, comprising:

a plurality of organic EL devices, wherein each organic EL device of the plurality of organic EL devices comprises:
a first electrode;
a second electrode;
an organic layer between the first electrode and the second electrode, wherein the organic layer includes:
a hole supply layer on the second electrode;
a plurality of light-emitting layers;
an electron supply layer on a first light-emitting layer of the plurality of light-emitting layers, wherein the electron supply layer includes a first layer and a second layer; and
a connecting layer between the first light-emitting layer and a second light-emitting layer of the plurality of light-emitting layers, wherein
the connecting layer includes a laminated structure, and
the laminated structure includes an electronic donor layer that has an electronic donor property, and an electronic acceptor layer that has an electronic acceptor property;
a plurality of light emission regions on the second electrode; and
an insulating layer on the second electrode, wherein
each light emission region of the plurality of light emission regions corresponds to an opening in the insulating layer,
a length of a diameter of the opening of the insulating layer is similar to a thickness of the insulating layer,
a thickness of the first layer is greater than a thickness of the hole supply layer,
the first layer contains a polycyclic aromatic hydrocarbon compound having an orientation, and
the second layer contains a larger amount of nitrogen element than the first layer.

* * * * *